(12) United States Patent
Mintchev et al.

(10) Patent No.: US 12,411,102 B2
(45) Date of Patent: Sep. 9, 2025

(54) SYSTEMS AND METHODS FOR VOLTAMMETRIC DETECTION

(71) Applicant: FREDsense Technologies Corp., Calgary (CA)

(72) Inventors: Paul Mintchev, Calgary (CA); Cheng Chen, Calgary (CA); Lisa Oberding, Calgary (CA); Robert Mayall, Calgary (CA); Mhairi McDonald, Cochrane (CA); Emily Hicks, Calgary (CA); Dylan Silver, Calgary (CA); Timothy Warrington, Cochrane (CA)

(73) Assignee: FREDsense Technologies Corp., Calgary (CA)

( * ) Notice: Subject to any disclaimer, the term of this patent is extended or adjusted under 35 U.S.C. 154(b) by 1040 days.

(21) Appl. No.: 17/421,940

(22) PCT Filed: Jan. 9, 2020

(86) PCT No.: PCT/CA2020/050022
§ 371 (c)(1),
(2) Date: Jul. 9, 2021

(87) PCT Pub. No.: WO2020/142845
PCT Pub. Date: Jul. 16, 2020

(65) Prior Publication Data
US 2022/0120705 A1 Apr. 21, 2022

Related U.S. Application Data

(60) Provisional application No. 62/791,352, filed on Jan. 11, 2019.

(51) Int. Cl.
*G01N 27/327* (2006.01)
*G01N 27/49* (2006.01)

(52) U.S. Cl.
CPC ......... *G01N 27/3272* (2013.01); *G01N 27/49* (2013.01)

(58) Field of Classification Search
CPC ......... B01L 2200/0647; B01L 2200/12; B01L 2200/16; B01L 2300/0645;
(Continued)

(56) References Cited

U.S. PATENT DOCUMENTS 5,658,531 A * 8/1997 Cope .................. G01N 21/0303
422/430
5,874,046 A 2/1999 Megerle
(Continued)

FOREIGN PATENT DOCUMENTS

CN 1350638 A 5/2002
CN 104854456 A 8/2015
(Continued)

OTHER PUBLICATIONS

International Search Report and Written Opinion mailed Mar. 24, 2020 in International Patent Application No. PCT/CA2020/050022 (9 pages).
(Continued)

*Primary Examiner* — Gurpreet Kaur
(74) *Attorney, Agent, or Firm* — SMART & BIGGAR LP; Tonino Rosario Orsi

(57) ABSTRACT

Cartridges for the voltammetric detection of fluid parameters in a fluid sample are provided. The cartridges contain a sample reservoir containing two compartments fluidically separated by a barrier. Each compartment contains a chemical compound to facilitate voltammetric detection of a fluid parameter. A fluid collection device containing a fluid sample can be received by the sample reservoir, and the barrier can be penetrated by the fluid collection device, to thereby cause contact between the fluid sample and both
(Continued)

chemical compounds. Upon introduction of the fluid sample in the sample reservoir a fluid parameter can be voltammetrically detected. Related assemblies including the cartridges, as well as methods for operating the cartridges are also described.

20 Claims, 23 Drawing Sheets

(58) Field of Classification Search
CPC ..... B01L 2300/0672; B01L 2400/0478; B01L 2400/0683; B01L 3/502; G01N 27/27; G01N 27/3272; G01N 27/49; G01N 33/1826
See application file for complete search history.

(56) References Cited

U.S. PATENT DOCUMENTS

| | | |
|---|---|---|
| 6,664,104 B2 | 12/2003 | Pourahmadi et al. |
| 6,964,862 B2 | 11/2005 | Chen |
| 7,863,035 B2 | 1/2011 | Clemens et al. |
| 9,114,399 B2 | 8/2015 | Laskowski et al. |
| 9,522,397 B2 | 12/2016 | Khattak et al. |
| 9,689,046 B2 | 6/2017 | Mayall et al. |
| 9,718,058 B2 | 8/2017 | Khattak et al. |
| 9,724,691 B2 | 8/2017 | Khattak et al. |
| 9,731,297 B2 | 8/2017 | Glezer et al. |
| 9,791,402 B2 | 10/2017 | Soleymani et al. |
| 10,022,720 B2 | 7/2018 | Shi et al. |
| 10,046,099 B2 | 8/2018 | White et al. |
| 2003/0170881 A1 | 9/2003 | Davis et al. |
| 2007/0166196 A1 | 7/2007 | Bardell et al. |
| 2008/0087554 A1 | 4/2008 | Norris et al. |
| 2008/0200343 A1 | 8/2008 | Clemens et al. |
| 2010/0029508 A1 | 2/2010 | Austin et al. |
| 2010/0167283 A1 | 7/2010 | Horgan et al. |
| 2011/0005932 A1 | 1/2011 | Jovanovich et al. |
| 2011/0304040 A1 | 12/2011 | Kojima |
| 2012/0178091 A1 | 7/2012 | Glezer et al. |
| 2012/0178179 A1 | 7/2012 | Kim et al. |
| 2014/0273054 A1 | 9/2014 | Franciskovich et al. |
| 2015/0259671 A1 | 9/2015 | Puleo et al. |
| 2016/0008811 A1 | 1/2016 | Laser et al. |
| 2016/0016172 A1 | 1/2016 | Pollack et al. |
| 2016/0038942 A1 | 2/2016 | Roberts |
| 2016/0091518 A1 | 3/2016 | Khattak et al. |
| 2016/0377573 A1 | 12/2016 | Kosugi et al. |
| 2017/0023512 A1 | 1/2017 | Cummins et al. |
| 2017/0045507 A1* | 2/2017 | Khattak ............ B65D 83/0817 |
| 2018/0100188 A1 | 4/2018 | Griessner et al. |
| 2018/0106791 A1 | 4/2018 | Gordon |
| 2018/0161769 A1 | 6/2018 | Kayyem et al. |
| 2018/0221872 A1 | 8/2018 | Boehm et al. |
| 2018/0265833 A1* | 9/2018 | Holder ................ C12M 27/00 |

FOREIGN PATENT DOCUMENTS

| | | |
|---|---|---|
| JP | 3633237 B2 | 3/2005 |
| WO | 9731264 A1 | 8/1997 |
| WO | 2017040946 A1 | 3/2017 |

OTHER PUBLICATIONS

Extended European Search Report mailed Jul. 8, 2022 in European Patent Application No. 20738477.7 (10 pages).

Yong et al., Quantum dot-based electrochemical biosensors Detection of tumors and its markers, Journal of Taishan Medical College, vol. 34 No 10 (2013) (9 pages).

Yiming, Study of a highly sensitive electrochemical detection method for tumor markers, Journal of Qingdao University of Science and Technology (Natural Science Edition), vol. 39, Supplement 1, 2018 (4 pages).

* cited by examiner

FIG. 4A  FIG. 4B

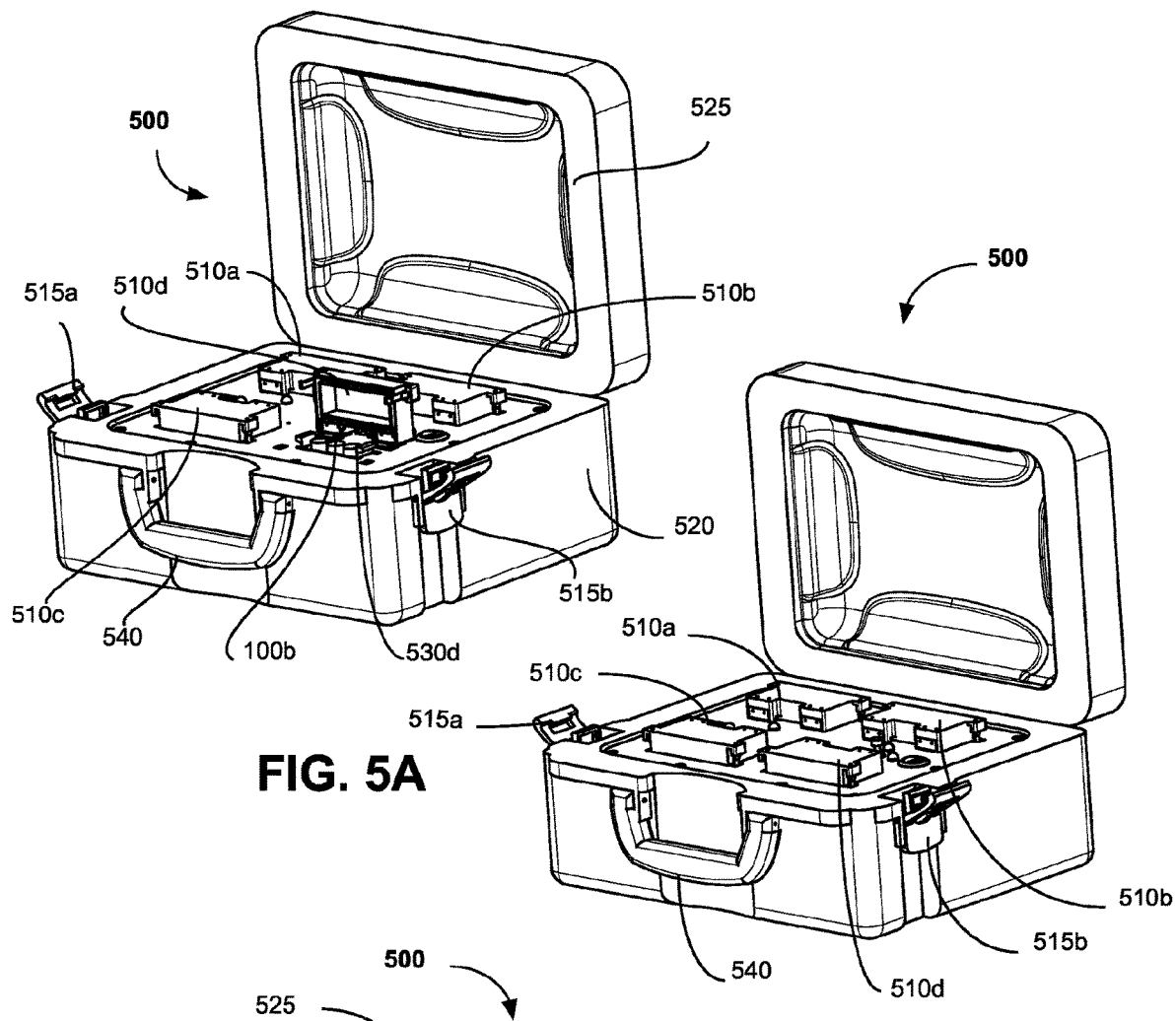
FIG. 5A
FIG. 5B
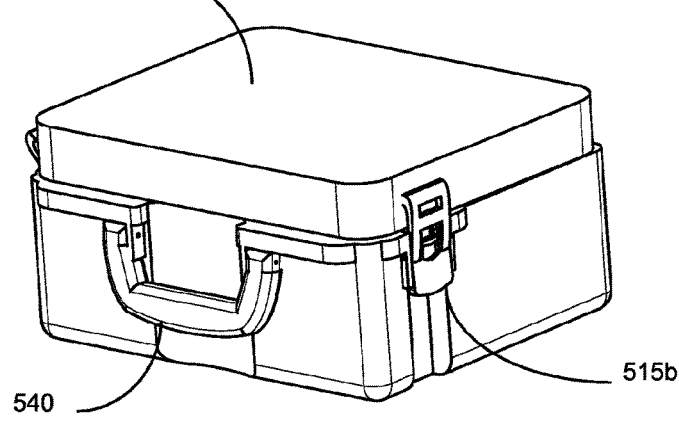
FIG. 5C

SYSTEMS AND METHODS FOR VOLTAMMETRIC DETECTION

RELATED APPLICATION

This application is a 35 USC § 371 national stage entry of International Patent Application No. PCT/CA2020/050022, filed Jan. 9, 2020, which claims the benefit of U.S. Provisional Patent Application No. 62/791,352, filed Jan. 11, 2019; the entire contents of each of which are hereby incorporated by reference.

FIELD OF THE DISCLOSURE

The present disclosure generally relates to voltammetric detection systems, and in particular to voltammetric systems and methods for the detection of fluid parameters in fluids.

BACKGROUND

The following paragraphs are provided by way of background to the present disclosure. They are not however an admission that anything discussed therein is prior art or part of the knowledge of persons skilled in the art.

There are many circumstances in which the detection of chemical species in fluids is desirable. Thus, for example, water can contain chemical substances which must be monitored and maintained within certain tolerances in order to ensure a safe supply of drinking water for domestic purposes. Similarly, non-potable water, for example, water for use in industrial production processes, must meet certain quality standards in order to be suitable for its intended purpose. Consequently, a variety of assays to monitor chemical species in water and other fluids has evolved.

One class of assays for the detection of chemical species in fluids relies on the use of voltammetry. In general, voltammetric assays involve the application of a voltage to a sample fluid containing an electrically active chemical species, and the subsequent detection and evaluation of an electrical current.

Ideally techniques and systems for the detection of chemical species in a fluid are sensitive and rapid. Although voltammetric technology can be highly sensitive, the performance of many voltammetric techniques requires the availability of laboratory facilities, and transportation, and possibly additionally storage, of fluid samples from the sampling location to the laboratory. Transportation of fluid samples can be time consuming, costly, and depending on the fluid, may include safety risks. Moreover, a fluid sample may undergo alteration in chemical constituency during the time that it is shipped or stored, and therefore the fluid sample may no longer be representative of the in situ constituency of the chemical species, at the time the voltammetric assay is performed. In particular, few, if any, voltammetric technologies involving biological molecules as sensors, are known to the art which permit the immediate performance of a voltammetric assay at the location at which the fluid sample is obtained.

Thus, despite the availability of a variety of techniques for the detection of chemical species in fluids, the known techniques are insufficiently effective. There is an ongoing need in the art for improved processes for detecting chemical species, and in particular there is a need for improved voltammetric systems.

SUMMARY

The following paragraphs are intended to introduce the reader to the more detailed description that follows and not to define or limit the claimed subject matter of the present disclosure.

In one broad aspect, the present disclosure relates to systems for the voltammetric detection of fluid parameters in a fluid.

Accordingly, in one aspect, in accordance with the teachings herein, the present disclosure provides, in at least one embodiment, a sample analysis cartridge for the voltammetric detection of a fluid parameter in a fluid sample, the cartridge comprising:

at least one sample analysis reservoir operable to receive an end portion of a fluid collection device that is used for the releasable collection of the fluid sample, the sample analysis reservoir comprising:
a first compartment containing an activating compound or an electroactive analyte that is activatable by the activating compound when the activated compound is activated by the fluid parameter in the fluid sample to form an activated electroactive analyte, the first compartment having an opening and an upper end;
a second compartment containing the electroactive analyte that is activatable by the activated activating compound to form the activated electroactive analyte when the first compartment contains the activating compound, or the second compartment contains the activating compound when the first compartment contains the electroactive analyte; and
a penetrable barrier disposed between the first and second compartments to fluidically separate the first and second compartment; and
a voltammetric sensor disposed at least partially within the second compartment.

In at least one embodiment, during use, (i) when the first compartment contains an activating compound when the sample fluid is in the sample analysis reservoir and makes contact with the activating compound, the fluid parameter in the fluid sample can activate the activating compound and when the barrier is ruptured thereafter the activated activating compound can contact the electroactive analyte to form the activated electroactive analyte which in turn can generate an electrical signal that is detected by the voltammetric sensor allowing the presence of the fluid parameter to be detected when a voltage is applied across the sample analysis reservoir, or (ii) when the first compartment contains the electroactive analyte and the sample fluid is in the sample analysis reservoir and the barrier is ruptured thereafter the fluid parameter in the fluid sample can activate the activating compound in the second compartment, the activated activating compound can then contact the electroactive analyte to form the activated electroactive analyte which in turn can generate an electrical signal that is detected by the voltammetric sensor allowing the presence of the fluid parameter to be detected when a voltage is applied to the voltammetric sensor.

In at least one embodiment, the cartridge can comprise a cartridge housing comprising a bottom housing portion and a top housing portion, the first compartment being disposed within the top housing portion and the second compartment being disposed within the bottom housing portion.

In at least one embodiment, the cartridge can comprise a cartridge housing comprising a bottom housing portion, the penetrable barrier being disposed within the bottom housing portion to form the second compartment; and a top housing portion that is slidably coupled to the bottom housing portion to form the first compartment.

In at least one embodiment, the cartridge can include a second penetrable barrier, the second penetrable barrier being disposed over the opening of the first compartment and comprising a material for allowing an end portion of a fluid collection device, upon sufficient forceful engagement, to penetrate therethrough and be received by the first compartment to deliver the sample fluid thereto.

In at least one embodiment, the sample analysis reservoir can comprise a slot between the first and second compartments to slidably receive the penetrable barrier and separate the first and second compartments.

In at least one embodiment, the penetrable barrier separating the first and second compartments can comprise a divot, wherein the divot can contain the activating compound or the electroactive analyte.

In at least one embodiment, the penetrable barrier separating the first and second compartments can be fabricated from a material that is tearable by the end portion of the fluid collection device.

In at least one embodiment, the penetrable barrier separating the first and second compartments can be fabricated from a material that is shatterable by the end portion of the fluid collection device.

In at least one embodiment, the penetrable barrier separating the first and second compartment can be fabricated from a material that is pierceable by the end portion of the fluid collection device.

In at least one embodiment, the cartridge can contain two, three, four, five or six sample reservoirs.

In at least one embodiment, at least two different sample reservoirs can be used to detect at least two different fluid parameters.

In at least one embodiment, at least two different sample reservoirs can be used to detect at least two identical fluid parameters.

In at least one embodiment, the activating compound can be a compound which in prolonged contact with the electroactive analyte can cause sufficient activation of the electroactive analyte to be voltammetrically detectable in the absence of a fluid parameter from the sample fluid.

In at least one embodiment, the prolonged contact can be from about 10 minutes to about 120 minutes.

In at least one embodiment, the activating compound can be an activating polypeptide.

In at least one embodiment, the activating compound can be an activating polypeptide formed by cells, the cells comprising a promoter inducible by the fluid parameter and controlling the expression of an activating polypeptide.

In at least one embodiment, the cells can comprise microbial cells.

In at least one embodiment, the microbial cells can be bacterial cells or yeast cells.

In at least one embodiment, the microbial cells can be in a liquid form.

In at least one embodiment, the microbial cells can be in a dry form.

In at least one embodiment, the microbial cells can be in a gel form.

In at least one embodiment, the microbial cells can comprise spore cells.

In at least one embodiment, the microbial cells can comprise *Escherichia* cells.

In at least one embodiment, the microbial cells can comprise *Bacillus* cells.

In at least one embodiment, the cells can comprise microbial cells, and the activating polypeptide can be a hydrolase.

In at least one embodiment, the cells can comprise microbial cells, and the activating polypeptide can be a phosphatase.

In at least one embodiment, the hydrolase can be a selected from the group consisting of a β-galactosidase, β-glucuronidase and β-glucosidase.

In at least one embodiment, the electroactive analyte can be chlorophenol red-β-D-galactopyranoside (CPRG) and the activating compound can be β-galactosidase and when there is contact between the electroactive analyte and the activating compound chlorophenol red (CPR) is formed; or the electroactive analyte can be para-nitrophenol-β-D-glucuronide (PNPG) and the activating compound can be β-glucuronidase and when there is contact between the electroactive analyte and the activating compound, paranitrophenol (PNP) is formed; or the electroactive analyte can be para-di-phenol-β-D-glucopyranoside (PDPG) and the activating compound can be β-glucosidase and when there is contact between the electroactive analyte and the activating compound para-di-phenol (PDP) is formed; the electroactive analyte can be para-aminophenol-β-galactopyranoside (PAPG) and the activating compound can be β-galactosidase and when there is contact between the electroactive analyte and the activating compound para-aminophenol (PAP) is formed; or the electroactive analyte is para-aminophenyl phosphate (PAPP) and the activating compound is a phosphatase and when there is contact between the electroactive analyte and the activating compound para-aminophenol (PAP) is formed.

In at least one embodiment, the fluid parameter can be a physical fluid parameter.

In at least one embodiment, the fluid parameter can be a chemical substance.

In at least one embodiment, the chemical substance can be an organic chemical compound.

In at least one embodiment, the chemical substance can be an inorganic chemical compound.

In at least one embodiment the fluid parameter can be a toxic chemical substance.

In another aspect, the present disclosure provides, in at least one embodiment, a method of voltammetrically detecting a fluid parameter in a fluid, the method comprising:
providing a fluid sample comprising a fluid parameter, the fluid sample being releasably collectable in a fluid collection device;
inserting an end portion of the fluid collection device into a cartridge comprising:
at least one sample analysis reservoir operable to receive the end portion of a fluid collection device, the sample analysis reservoir comprising:
a first compartment containing an activating compound when the activated compound is activated by the fluid parameter in the fluid sample or an electroactive analyte that is activatable by the activating compound to form an activated electroactive analyte, the first compartment having an opening at the upper end;
a second compartment containing the electroactive analyte that is activatable by the activating compound to form the activated electroactive analyte when the first compartment contains the activating compound, or the second compartment containing the activating compound when the first compartment contains the electroactive analyte; and a penetrable barrier disposed between the first and second compartments to fluidically separate the first and second compartment; and a voltammetric sensor disposed at least partially within the second compartment;

moving the end portion of the fluid collection device into the first compartment and penetrating the barrier with the end portion of the fluid collection device to fluidically connect the first and second compartment, and releasing the fluid sample from the fluid collection device into the sample analysis reservoir causing the fluid parameter to activate the activating compound to create the activated activating compound which then contacts the electroactive analyte to thereby form the activated electroactive analyte which then contacts the voltammetric sensor;

applying a voltage to the voltammetric sensor;

detecting a current passing through the voltammetric sensor; and comparing the detected current to a threshold to determine a presence the fluid parameter in the fluid sample.

In at least one embodiment, the fluid sample can be released in the first compartment prior to penetrating the barrier when the first compartment contains the activating compound.

In at least one embodiment, the fluid sample can be released in the second compartment after penetrating the barrier when the second compartment contains the activating compound.

In at least one embodiment, the first compartment contains a second penetrable barrier being disposed over the opening, and the method comprises moving the fluid collection device sufficiently forcefully to penetrate the second barrier and move into the first compartment.

In another aspect, the present disclosure provides, in at least one embodiment, a method of manufacturing a sample analysis cartridge for the voltammetric detection of a fluid parameter in a fluid sample, the method comprising:

forming one or more sample reservoirs for the sample analysis cartridge where each sample reservoir is made by:

forming a bottom cartridge housing portion having a voltammetric sensor disposed therein;

placing an electroactive analyte or an activating compound in the bottom cartridge housing portion;

forming a top cartridge housing portion;

forming a penetrable barrier to separate the bottom and top cartridge housing portions;

placing an activating compound in the top cartridge housing portion when an electroactive analyte is placed in the bottom cartridge housing portion, or placing the electroactive analyte in the top cartridge housing portion when the activating compound is placed in the bottom cartridge housing portion, on the penetrable barrier;

and (a) placing the penetrable barrier in the top portion of the bottom cartridge housing portion; and slidably coupling the bottom and top cartridge housing portions to thereby form a cartridge; or (b) slidably coupling the bottom and top cartridge housing portions to thereby form a cartridge comprising a slot between the bottom and top cartridge housing portions to slidably receive the penetrable barrier; and slidably inserting the penetrable barrier in the slot.

In at least one embodiment, the method can further include providing a second penetrable barrier, the second penetrable barrier being disposed over the opening of the top cartridge housing portion following the slidable coupling of the bottom and top cartridge housing portions.

In at least one embodiment, the penetrable barrier is formed comprising one or more divots to contain the activating compound or the electroactive analyte.

In at least one embodiment, the bottom housing compartment is formed comprising one or more divots to contain the electroactive analyte or activating compound.

In at least one embodiment, the penetrable barrier is formed from a material that is tearable by the end portion of the fluid collection device.

In at least one embodiment, the method comprises forming two, three, four, five or six sample reservoirs for the cartridge.

In another aspect, the present disclosure provides, in at least one embodiment, a voltammetric detection device for detecting a fluid parameter in a fluid sample contained in a sample analysis cartridge, the voltammetric detection device comprising:

at least one insertion slot for the releasable insertion of a sample analysis cartridge of the present disclosure;

a voltage source configured to apply a voltage to a voltammetric sensor in a reservoir of the sample analysis cartridge;

a current detector for detecting a current passing through the voltammetric sensor upon application of the voltage to the sensor; and a controller that is operatively coupled to the voltage source and the current detector and is configured to control the operation of the voltammetric detection device.

In at least one embodiment, the voltammetric detection device can comprise two, three, four, five or six insertion slots.

In at least one embodiment, the voltage detector can be operably coupled to a memory device.

In another aspect, the present disclosure provides, in at least one embodiment, a voltammetric detection assembly, the assembly comprising:

a voltammetric detection device comprising:

at least one insertion slot for the releasable insertion of a sample analysis cartridge of the present disclosure;

a voltage source configured to apply a voltage to a voltammetric sensor in a reservoir of the sample analysis cartridge;

a current detector for detecting a current passing through the voltammetric sensor upon application of the voltage to the sensor; and a controller that is operatively coupled to the voltage source and the current detector and is configured to control the operation of the voltammetric detection device; and a fluid collection device for releasably collecting fluid samples for insertion into the sample analysis cartridge.

In another aspect, the present disclosure provides, in at least one embodiment, a use of a sample analysis cartridge of the present disclosure for the voltammetric detection of a fluid parameter in a fluid sample.

Other features and advantages or the present disclosure will become apparent from the following detailed description. It should be understood, however, that the detailed description, while indicating preferred implementations of the present disclosure, is given by way of illustration only, since various changes and modification within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. Like numerals designate like or similar features throughout the several views possibly shown situated differently or from a different angle. Thus, by way of example only, part 200 in FIG. 2A, FIG. 3B and FIG. 3D refers to a fluid collection device in each of these figures. The figures are not intended to limit the present disclosure.

FIG. 4A is a vertical cross section of another cartridge in a first state.

FIG. 4B is a vertical cross section of the cartridge of FIG. 4B in a second state.

FIG. 5A is a perspective view of a voltammetric detection device with a cartridge inserted in a cartridge holder showing the cartridge holder in an open position and the voltammetric detection device in an open position.

FIG. 5B is a perspective view of the voltammetric detection device of FIG. 5A with a cartridge inserted in a cartridge holder showing the cartridge holder in a closed position and the voltammetric detection device in an open position.

FIG. 5C is a perspective view of the voltammetric detection of FIG. 5A showing the voltammetric detection device in a closed position.

Figure 1A:
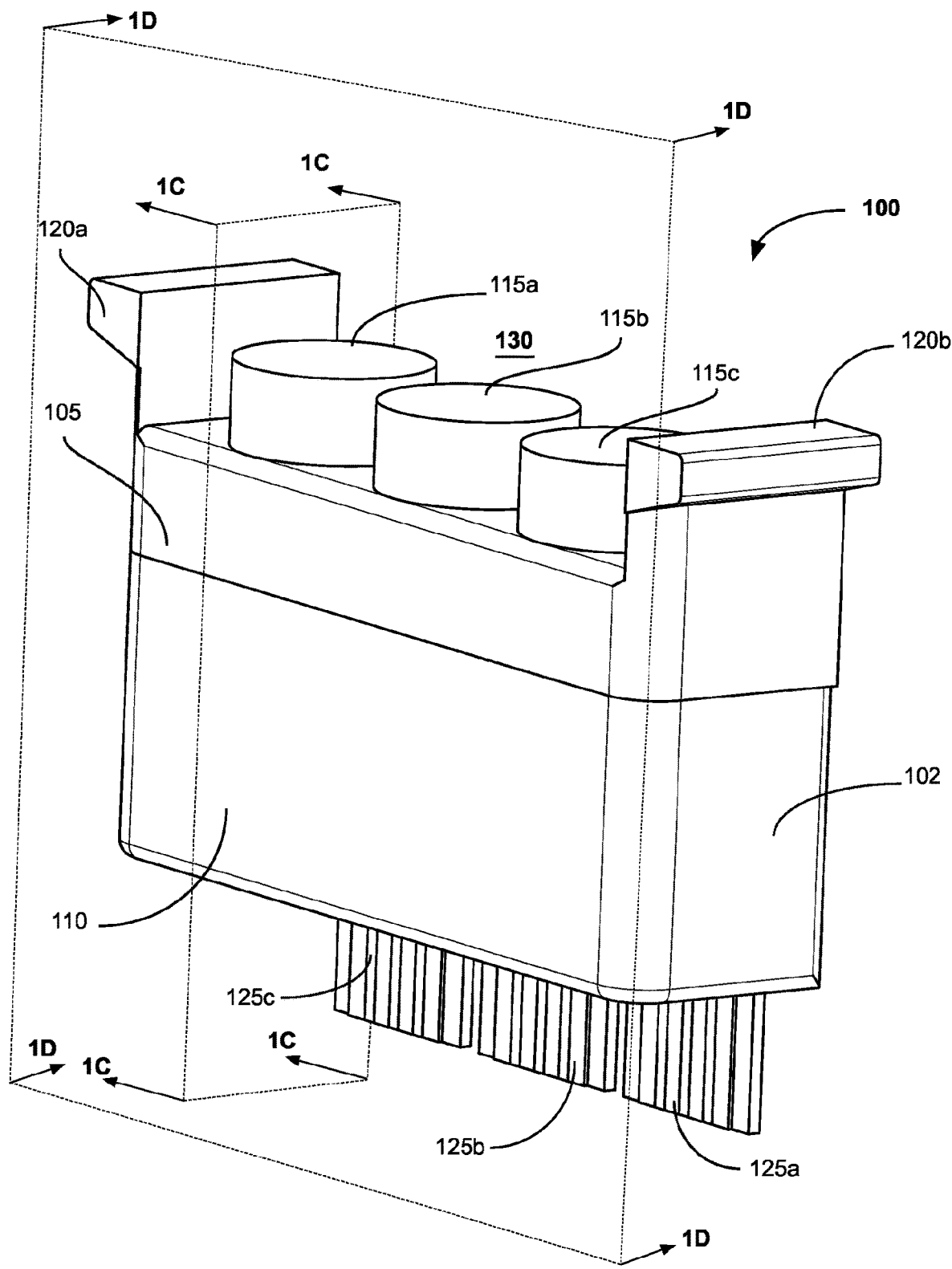
FIG. 1A is a perspective view of an example embodiment of a cartridge.

The figures together with the following detailed description make apparent to those skilled in the art how the disclosure may be implemented in practice.

DETAILED DESCRIPTION

Various processes, systems and compositions will be described below to provide at least one example of at least one embodiment of the claimed subject matter. No embodiment described below limits any claimed subject matter and any claimed subject matter may cover processes, systems, or compositions that differ from those described below. The claimed subject matter is not limited to any process, system, or composition having all of the features of processes, systems, or compositions described below, or to features common to multiple processes, systems, compositions or compositions described below. It is possible that a process, system, or composition described below is not an embodiment of any claimed subject matter. Any subject matter disclosed in processes, systems, or compositions described below that is not claimed in this document may be the subject matter of another protective instrument, for example, a continuing patent application, and the applicants, inventors or owners do not intend to abandon, disclaim or dedicate to the public any such subject matter by its disclosure in this document.

As used herein and in the claims, the singular forms, such as "a", "an" and "the" include the plural reference and vice versa unless the context clearly indicates otherwise. Throughout this specification, unless otherwise indicated, the terms "comprise," "comprises" and "comprising" are used inclusively rather than exclusively, so that a stated integer or group of integers may include one or more other non-stated integers or groups of integers. The term "or" is inclusive unless modified, for example, by "either". The term "and/or" is intended to represent an inclusive or. That is "X and/or Y" is intended to mean X or Y or both, for example. As a further example, X, Y and/or Z is intended to mean X or Y or Z or any combination thereof.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as being modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by the context. Furthermore, any range of values described herein is intended to specifically include the limiting values of the range, and any intermediate value or sub-range within the given range, and all such intermediate values and sub-ranges are individually and specifically disclosed (e.g. a range of 1 to 5 includes 1, 1.5, 2, 2,75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term, such as up to 15% for example, if this deviation would not negate the meaning of the term it modifies.

Several directional terms such as "above", "below", "lower", "upper", "inner" and "outer" are used herein for convenience including for reference to the drawings. In general, the terms "upper", "above", "upward" and similar terms are used to refer to an upwards direction or upper portion in relation to a cartridge generally held upright, for example, such as shown in the orientation shown in FIG. 1A. Similarly the terms "lower", "below", "downward", and "bottom" are used to refer to a downwards direction or a lower portion in relation to a cartridge generally held upright, for example, such as shown in the orientation shown FIG. 1A. The terms "inner" and "inward" are used herein to refer to a direction that is more radially central relative to a generally central longitudinal axis of a component, while the terms "outer" and "outward" refer to a direction that is more radially peripheral relative to the generally central longitudinal axis of a component.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents, and patent applications referred herein are herein incorporated by reference in their entirety to the same extent as if each individual publication, patent or patent application was specifically indicated to be incorporated by reference in its entirety.

In general, the sample analysis cartridge of the present disclosure can be used to detect a fluid parameter present in a fluid sample, for example, a physical or a chemical fluid parameter.

In broad terms, the sample analysis cartridge includes a sample analysis reservoir, in which a fluid sample can be received. The sample analysis reservoir contains an electroactive analyte which can be activated by a fluid parameter. Notably, the activation can proceed via an intermediate activating compound also contained in the sample analysis reservoir. Disposed in the cartridge is further a voltammetric sensor. Upon contact between the activated electroactive analyte and the voltammetric sensor an electrical signal can be generated. The cartridge can be situated in a voltammetric detection device to allow for detection of the electrical signal indicative of the presence of the fluid parameter in the fluid sample.

The cartridge of the present disclosure can be used in conjunction with a hand held voltammetric detection device. Accordingly, the herein provided cartridge, together with the voltammetric detection device and fluid collection device, permits the evaluation for the presence of fluid parameters in a fluid sample at a location that is in close proximity of the fluid sampling site. One challenge with many known voltammetric systems is that they are operable only in a laboratory. Thus transport of the fluid sample from the sampling site to the laboratory is required. The time delay between sampling and analysis can impact the accuracy of the analysis. Further, depending on the sample fluid, there may be safety considerations associated with transport and storage of the sample fluid. Furthermore, transport and storage of sample fluids may be costly.

By contrast, the cartridge of the present disclosure can be deployed at the fluid sampling site, and can provide rapid analysis results at the sampling site without the need for transportation or storage of sample fluids, or the need for additional laboratory equipment.

Furthermore, the cartridge of the present disclosure does not require mixing of reagents involving multiple fluid transfer steps. Instead, the cartridge permits a user to obtain assay results using a single fluid transfer step, namely the transfer of sample fluid to the cartridge.

In what follows selected embodiments are described with reference to the drawings.

Figure 6:
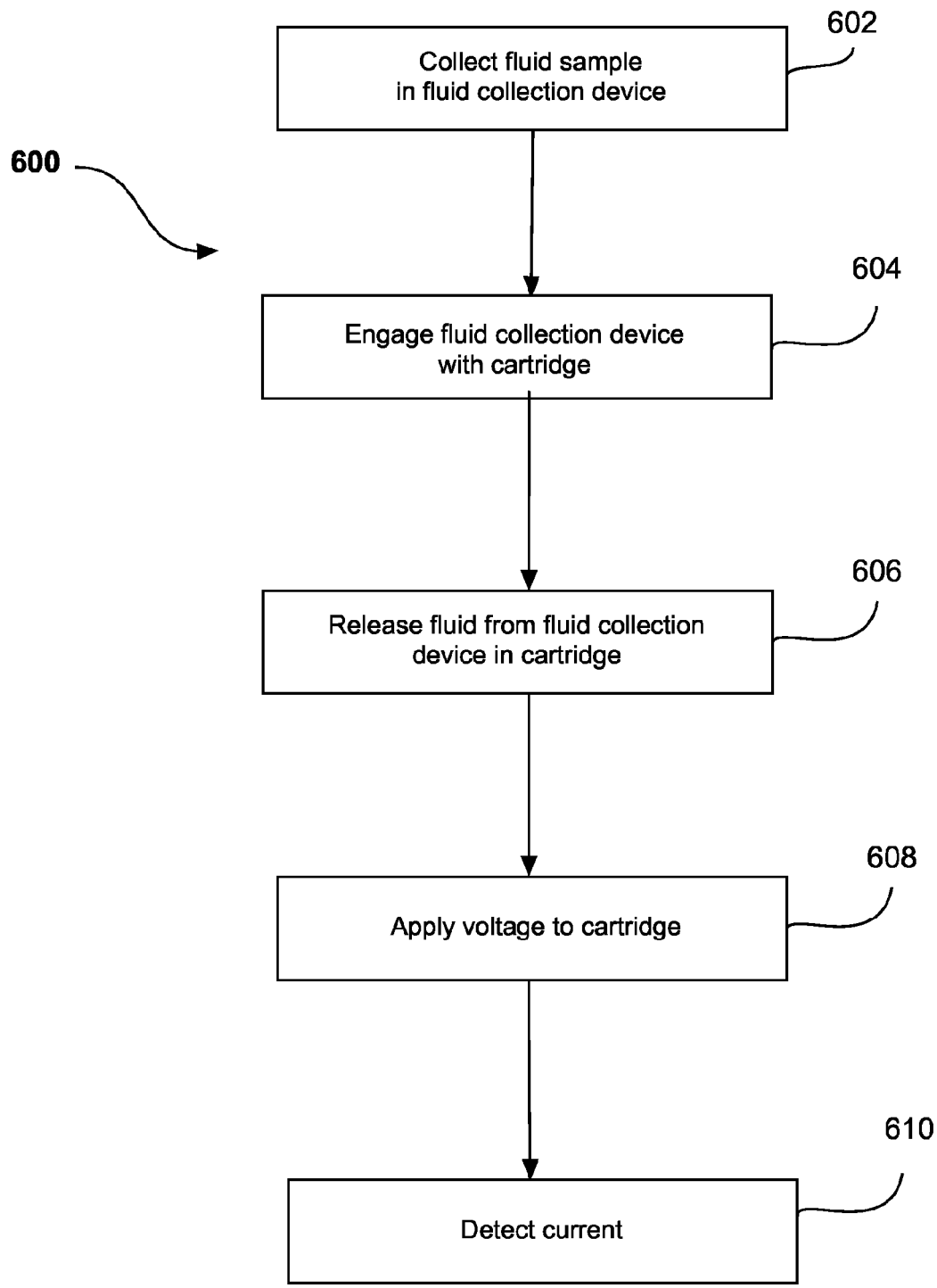
FIG. 6 is a flow chart showing an example embodiment of a method for voltammetrically detecting a fluid parameter using the cartridge of FIGS. 1A-D and the fluid collection device of FIGS. 2A-C, in accordance with the teachings herein.
Figure 7:
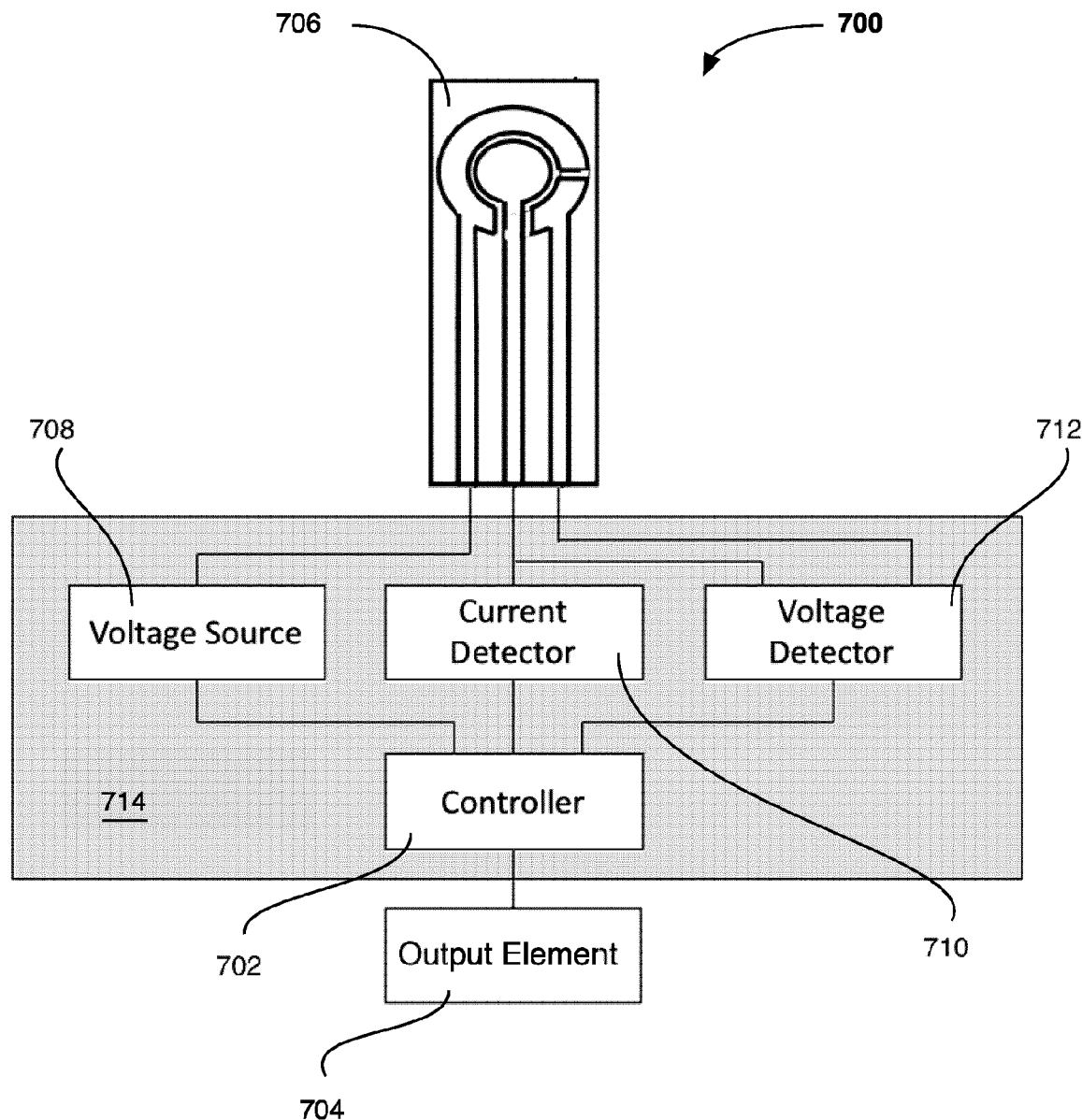
FIG. 7 is a block diagram showing an example embodiment of a configuration of a voltammetric detection device.
Figure 9:
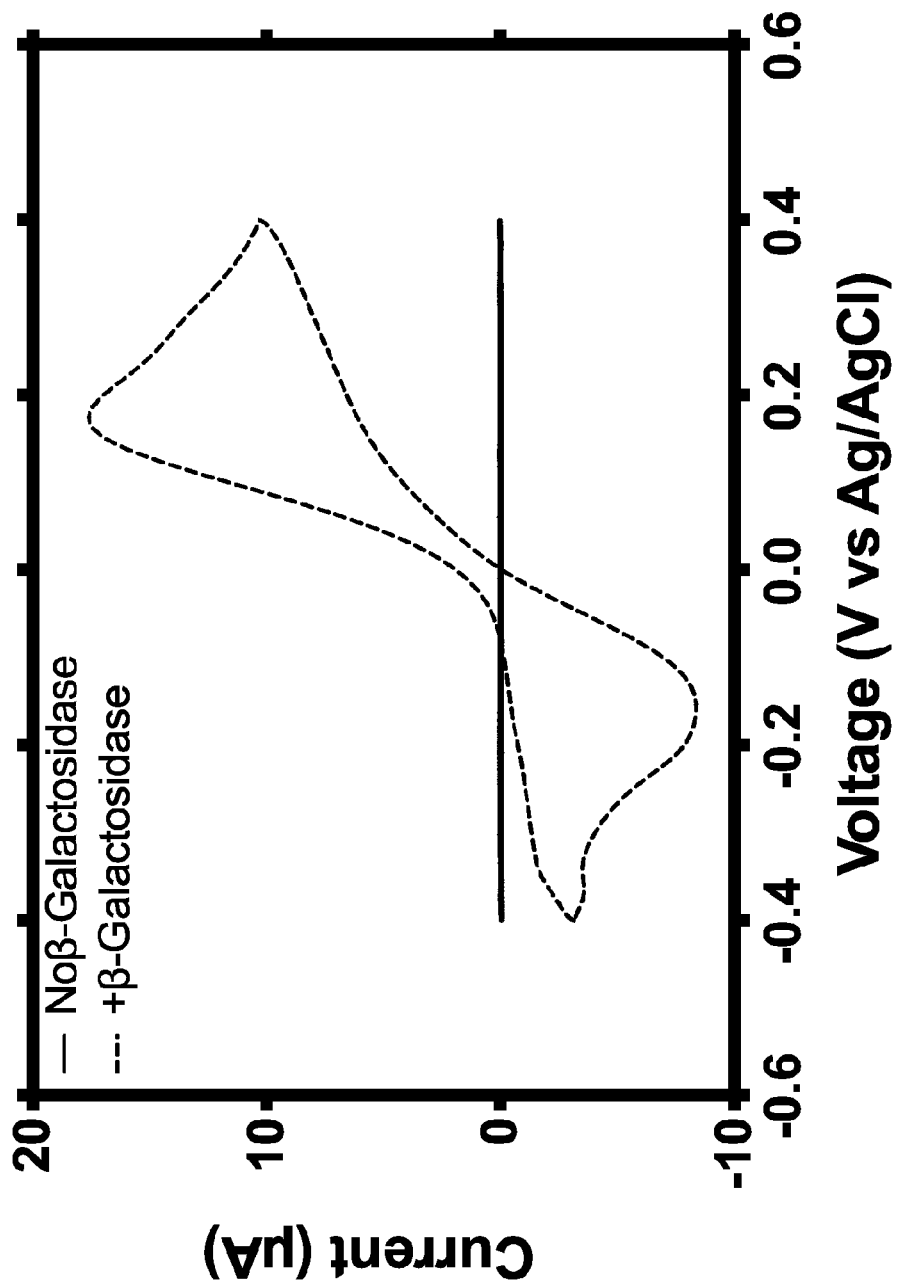
FIG. 9 is a voltammetry graph illustrating experimental results obtained using an example embodiment of a cartridge and a voltammetric detection device of the present disclosure.
Figure 10:
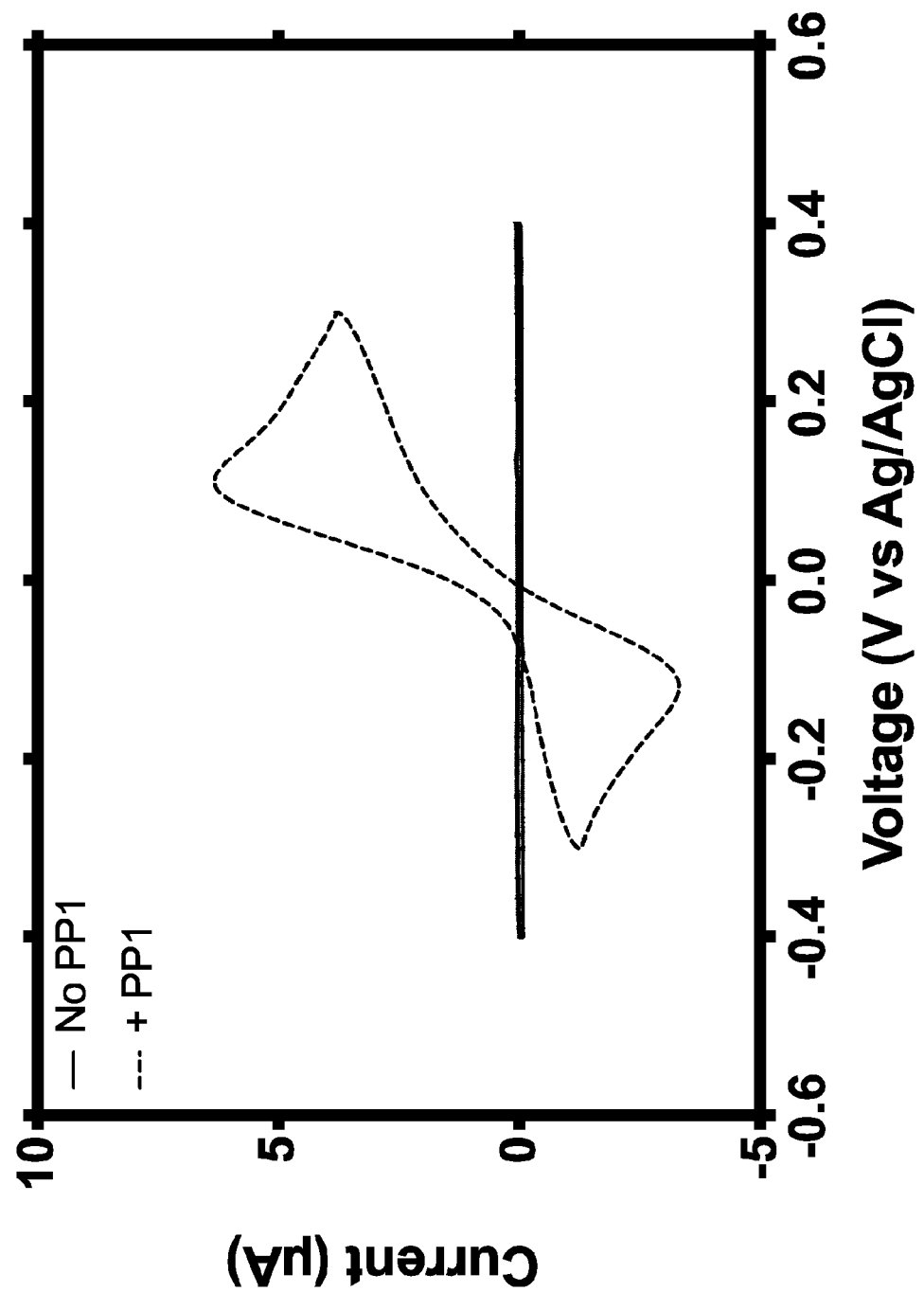
FIG. 10 is another voltammetry graph illustrating experimental results obtained using an example embodiment of a cartridge and a voltammetric detection device of the present disclosure.
Figure 11:
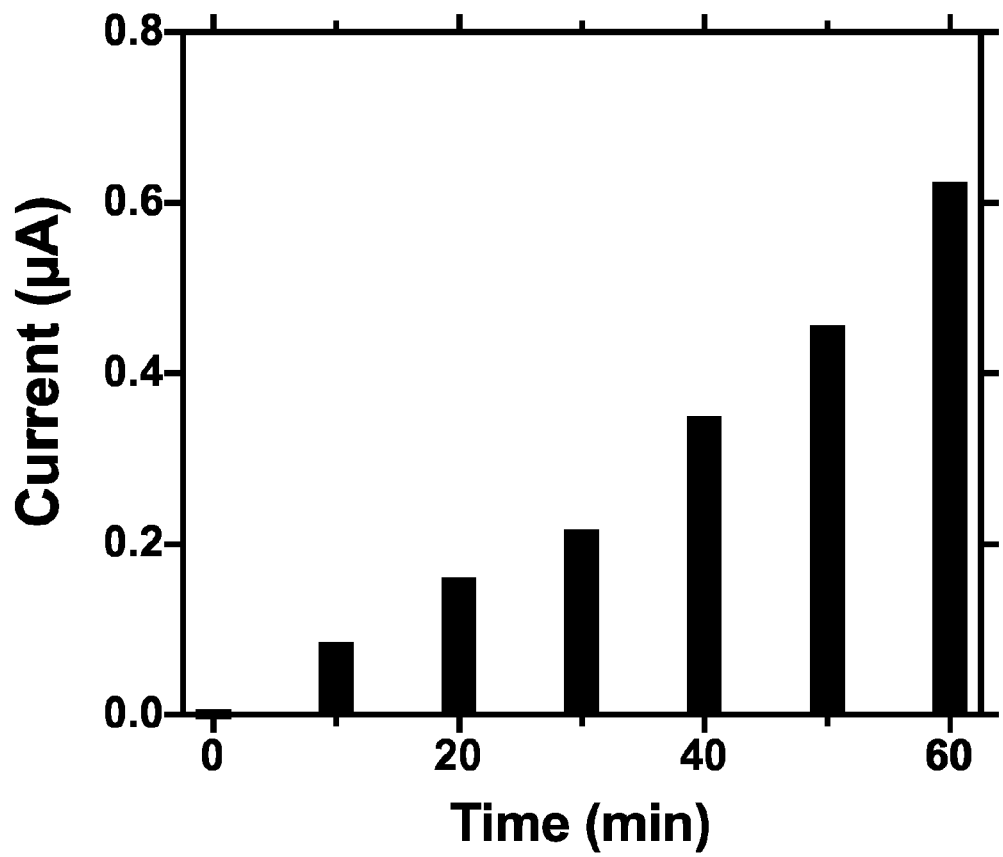
FIG. 11 is a bar graph illustrating experimental results obtained using a cartridge comprising a sample analysis reservoir comprising a single compartment and a voltammetric detection device.

In general overview, FIGS. 1A-1D show several views of an example embodiment of a cartridge 100. FIGS. 2A-2C show several views of an example embodiment of a fluid collection device 200 for use in conjunction with cartridge 100. FIGS. 3A-3D show cartridge 100 in operation in conjunction with fluid collection device 200. FIGS. 4A-4B show several views of another example cartridge 300. FIG. 4C shows an example embodiment of a penetrable barrier, which is a component of a cartridge described herein. FIGS. 5A-5C and FIG. 8A-8B show several views of cartridge 100 in operation in conjunction with an example voltammetric detection device 500. FIG. 6 shows a flow chart of an example method 600 of operating cartridge 100 together with fluid collection device 200. FIG. 7 shows a block diagram of an example configuration of a voltammetric detection device. FIGS. 9, 10, and 12-18 show graphs illustrating various experimental results obtained using cartridge 100, while FIG. 11 shows a graph illustrating results using an alternate cartridge, as further described in the Example section of the present disclosure.

Figures 2A, 2B, 2C:
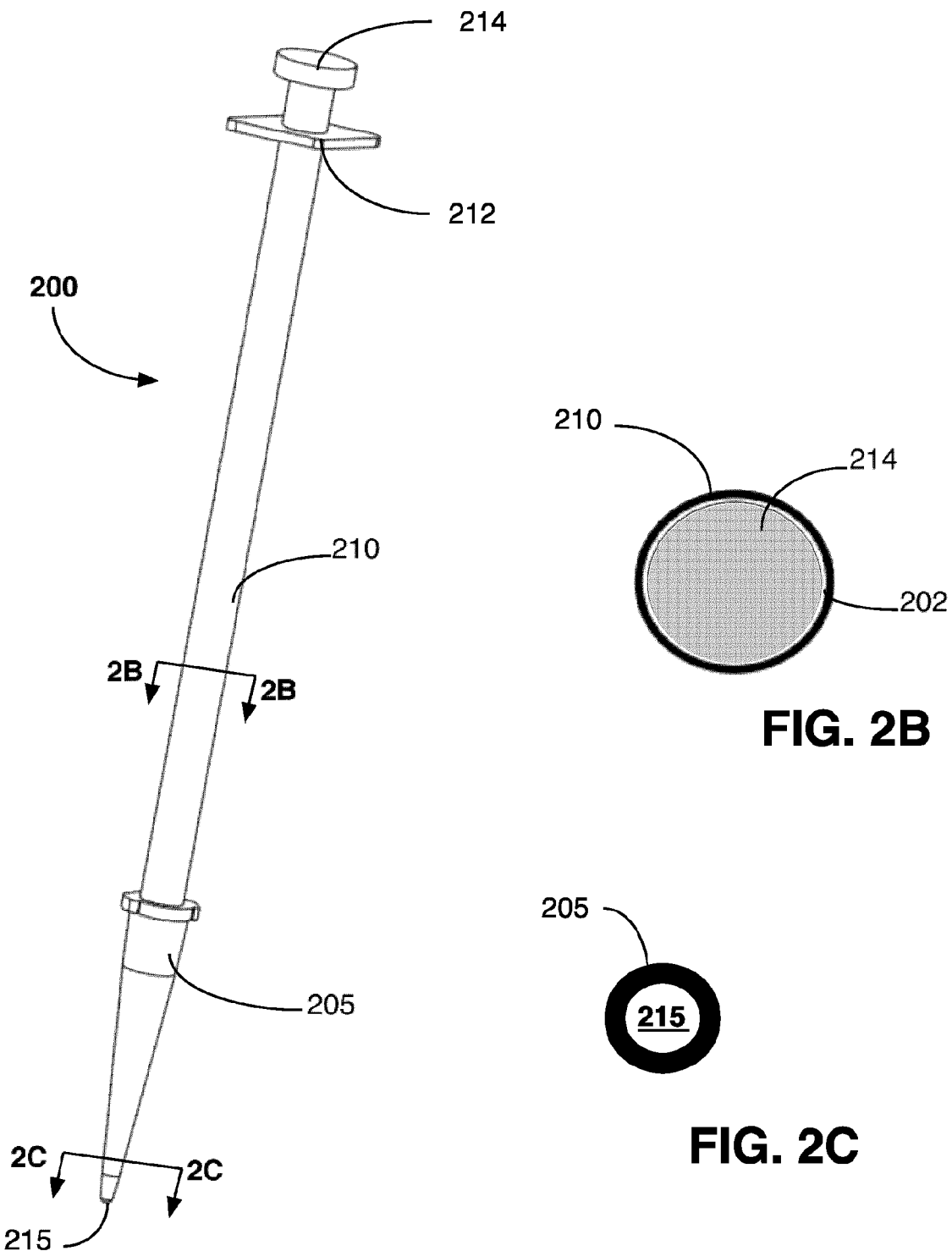
FIG. 2A is a perspective view of an example embodiment of a fluid collection device.
FIG. 2B is a horizontal cross-section view of the fluid collection device taken along the plane 2B in FIG. 2A.
FIG. 2C is a horizontal cross-section view of the fluid collection device taken along the plane 2C in FIG. 2A.

Referring initially to FIG. 1A, shown therein is example cartridge 100 for the voltammetric detection of sample fluids. Cartridge 100 includes housing 102 comprising top housing portion 105 and bottom housing portion 110. Top housing portion 105 and bottom housing portion 110 facilitate manufacturing and assembly of cartridge 100, including the introduction of certain chemical compounds in cartridge 100, as hereinafter further described. Top housing portion 105 includes grip components 120*a* and 120*b* to facilitate manipulation of cartridge 100. Housing 102 is further configured to form three sample analysis reservoirs (not visible in FIG. 1A) disposed within cartridge 100. Each sample analysis reservoir has a top opening (also not visible in FIG.

1A), and each sample analysis reservoir is covered by penetrable barriers 115a, 115b and 115c, separating each sample analysis reservoir from exterior 130. It is noted that in other embodiments, it is possible to configure a cartridge including one or more sample analysis reservoirs without a penetrable barrier covering the opening of such one or more sample analysis reservoirs. Furthermore, in other embodiments, the cartridges of the present disclosure can include fewer (1 or 2), or more (e.g. 4, 5, 6) sample analysis reservoirs. Also shown are voltammetric sensors 125a, 125b and 125c, each associated with one of the three sample reservoirs, as can be better seen in FIG. 1B. A variety of voltammetric sensors suitable for voltammetric detection can be used in various embodiments hereof. Some example voltammetric sensors are hereinafter described.

Figure 1B:
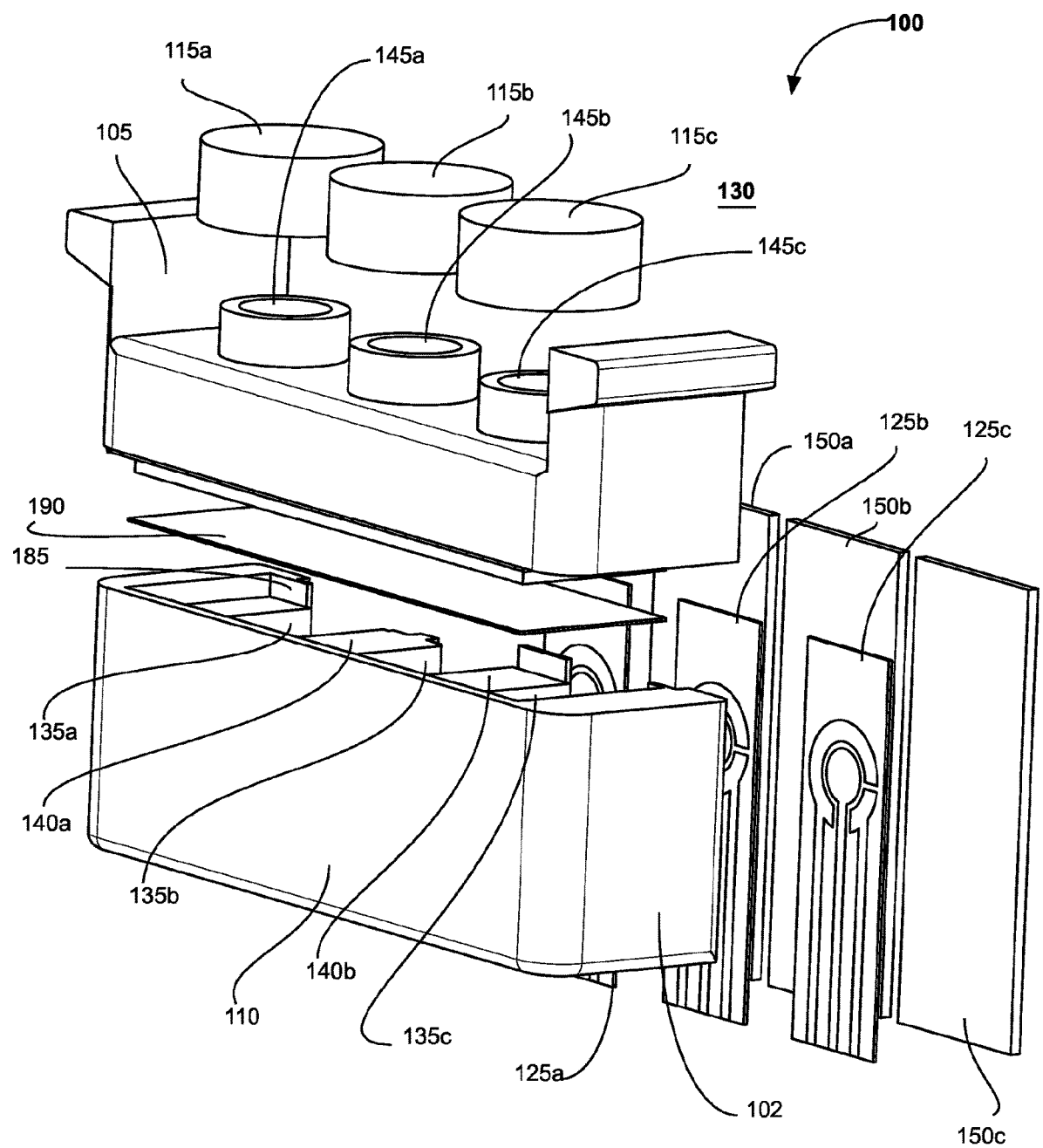
FIG. 1B is an exploded perspective view of the cartridge of FIG. 1A.

Referring now to FIG. 1B, shown therein, is an exploded view of example cartridge 100. Shown, in addition to various parts shown in FIG. 1A, are sample reservoirs 135a, 135b, and 135c disposed within cartridge 100, and top openings 145a, 145b and 145c of each of sample reservoirs 135a, 135b and 135c, respectively. It is noted that when cartridge 100 is assembled with barriers 115a, 115b and 115c in place (as shown in FIG. 1A) there is no fluidic communication between the interior of sample analysis reservoirs 135a, 135b and 135c and exterior 130. Further, interior housing walls 140a and 140b separate sample reservoirs 135a and 135b, and 135b and 135c, respectively, from one another in such a manner that there also is no fluidic communication between any of sample reservoirs 135a, 135b and 135c. Further shown is penetrable barrier 190, which when installed, divides sample reservoirs 135a, 135b and 135c into a top and bottom portion, as can be better seen in FIG. 1C. In an alternate embodiment, three separate penetrable barriers, each sized to be sufficiently large to cover each of sample reservoirs 135a, 135b and 135c may be used. Further also shown are voltammetric sensors 125a, 125b and 125c of which, as can now be better appreciated, a major portion is disposed in sample reservoirs 135a, 135b and 135c, respectively, with bottom portions extending below the bottom housing portion 110. Situated to the exterior of voltammetric sensors 125a, 125b and 125c are conducting components 150a, 150b and 150c. When cartridge 100 is assembled conducting components 150a, 150b and 150c are electrically coupled with voltammetric sensors 125a, 125b and 125c, respectively. When in use for voltammetric analysis, conducting components 150a, 150b and 150c of cartridge one 100 can be electrically coupled to the electronic circuitry of the voltammetric detection device. Voltammetric sensors 125a, 125b and 125c, and conducting components 150a, 150b and 150c together are embedded in housing 102 to form at least a portion of exterior wall 185 of each of sample reservoirs 135a, 135b and 135c.

Figure 1C:
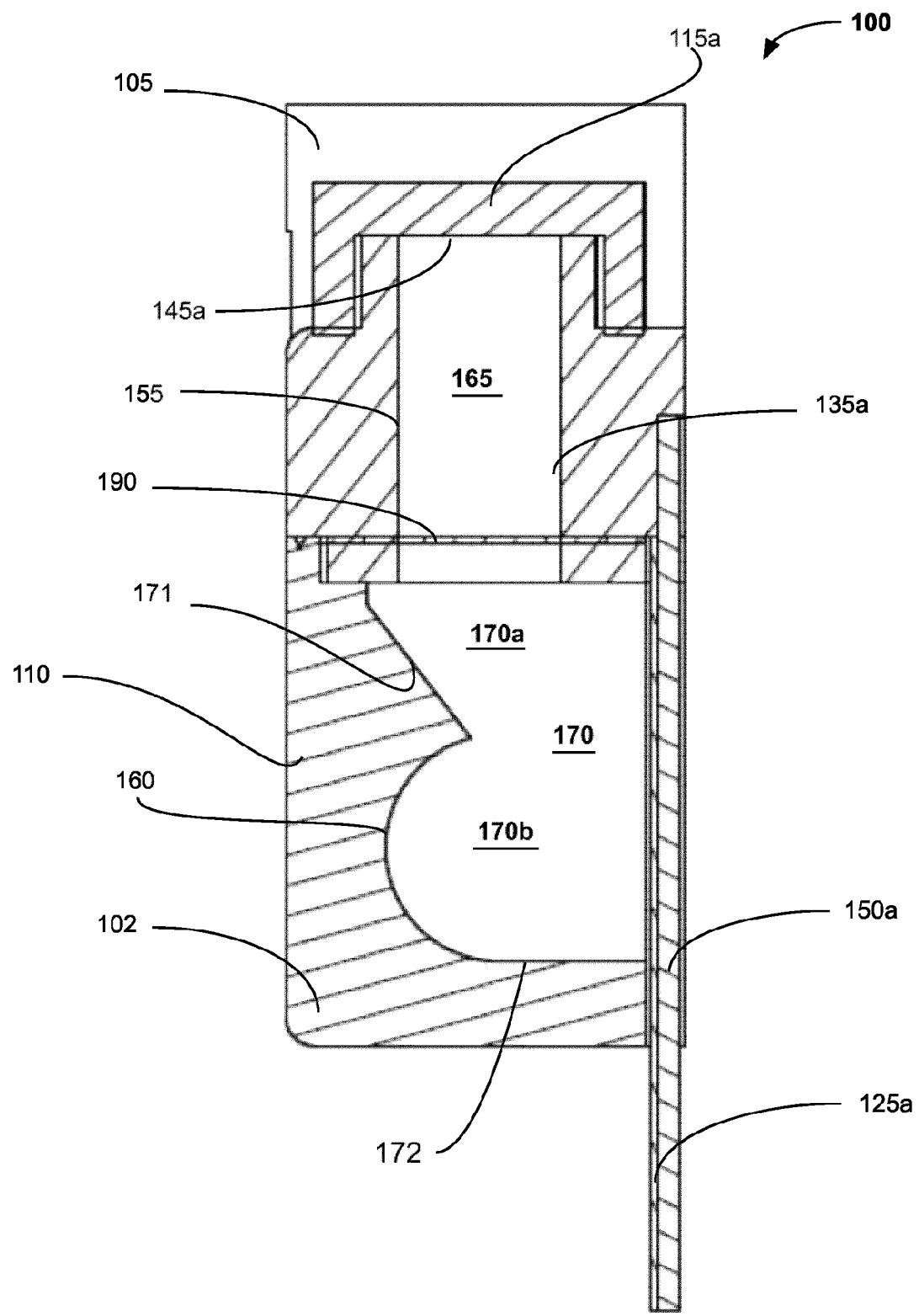
FIG. 1C is a vertical cross-section view of the cartridge taken along the plane 1C in FIG. 1A.

Referring now to FIG. 1C, shown therein is a cross sectional view of example cartridge 100. Shown besides several of the parts shown in FIGS. 1A-1B, is sample reservoir 135a, including top compartment 165 and bottom compartment 170, defined by interior surfaces 155 and 160, respectively. As hereinbefore mentioned, top compartment 165 and bottom compartment 170 are fluidically separated from one another by penetrable barrier 190. It is noted that the geometry of interior surfaces 155 and 160 may vary in different embodiments, such that, for example, the top and bottom compartments 165 and 170 can each be cylindrically, or approximately cylindrically shaped, or conically, or approximately conically shaped. In the shown embodiment, top portion 170a of bottom compartment 170 comprises a generally inward and downward angled sloping surface 171 which can function as a stop to prevent a fluid collection device from reaching into bottom portion 170b of bottom compartment 170, and further notably to prevent contact between bottom surface 172 of bottom portion 170b and the fluid collection device when the fluid collection device is being received in sample reservoir 135a, to thereby facilitate fluid release from the fluid collection device, as hereinafter further described. In general, the geometry of interior surfaces 155 and 160 is designed such that a fluid collection device can be received within sample reservoir 135a to release a fluid sample, as hereinafter described. Furthermore, curved interior surface area 160, extending downward and outward from inward and downward angled surface 171, can facilitate receipt and containment of an electroactive analyte in bottom portion 170b of bottom compartment 170, in particular when the electroactive analyte is provided in liquid form. Furthermore, it is noted that the interior volumes of top compartment 165 and bottom compartment 170 can vary in different embodiments. In some embodiments, relative volumes of top and bottom compartments are somewhat similar, for example, about 1:1, 1:2, 1:3, 1:4, or 4:1 3:1, 2:1, or 1:1. In further embodiments, the total volume of sample reservoir 135a, can range, for example, from about 250 µl to about 5,000 µl.

Figure 1D:
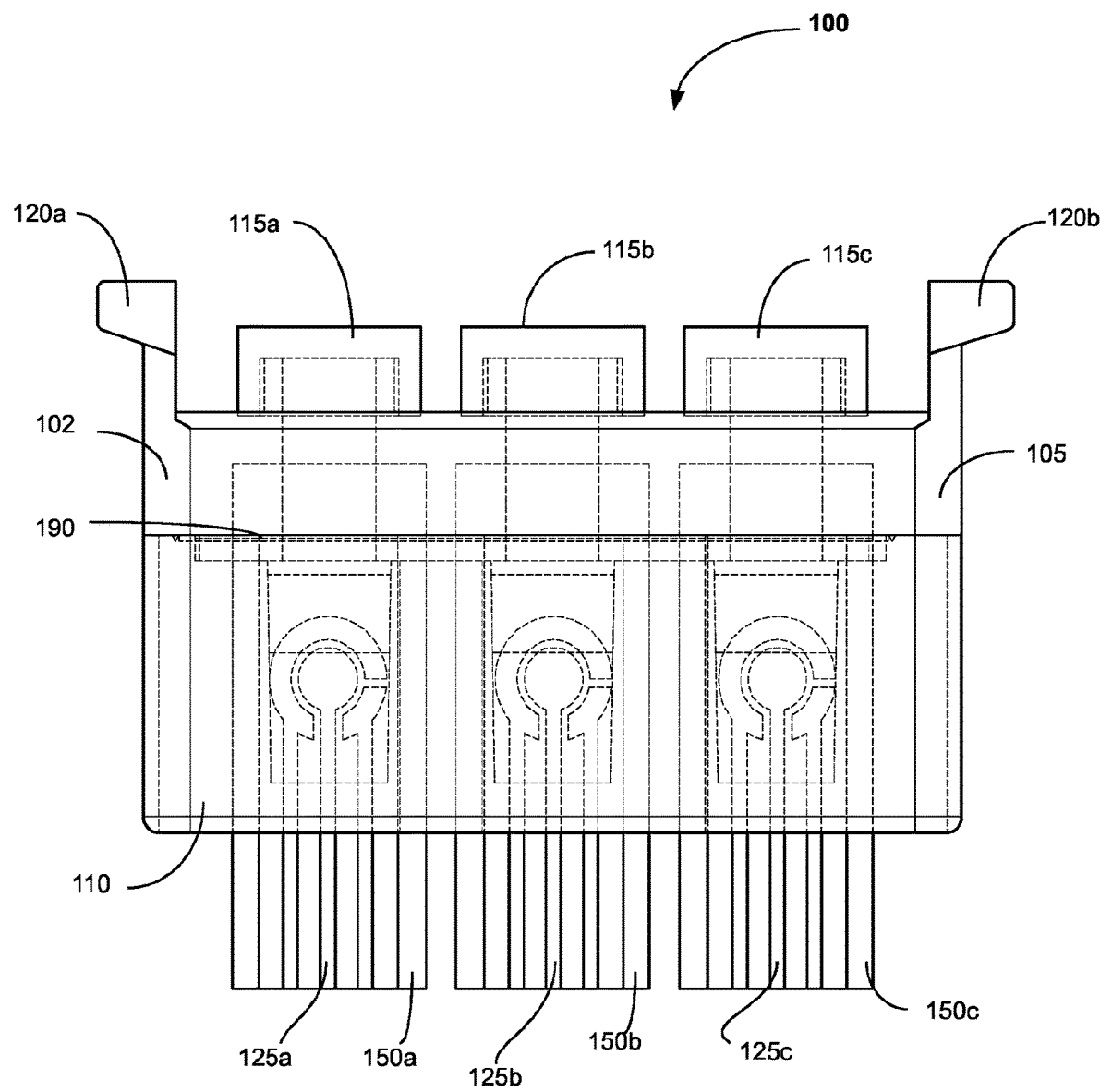
FIG. 1D is a side view of the cartridge of taken along the plane 1D in FIG. 1A.

Referring now to FIG. 1D, shown therein is, for further clarity, is a cross-section of example cartridge 100, indicating several of the parts shown in FIGS. 1A-1C.

Referring now to FIGS. 2A-C, shown therein is an example embodiment of a fluid collection device 200 for use in conjunction with the cartridges of the present disclosure. Fluid collection device 200 comprises fluid reservoir portion 210, which is defined by inner bore 202, and extends downwards towards tip portion 205 containing downward tapering tip reservoir portion 207 (see FIG. 3A). Tip portion 205 can be received by a cartridge, as hereinafter described. Fluid reservoir portion 210 further includes finger rest 212 and plunger 214. Plunger 214 is movable in upward and downward directions within bore 202 of fluid reservoir portion 210. As will be readily appreciated by to those of skill in the art, upward movement of plunger 214, if tip portion 205 is immersed in a fluid, will allow the fluid to be drawn up through opening 215 into tip reservoir portion 207 of tip portion 205, and from there into inner bore 202. Conversely, when fluid is present in inner bore 202, downward movement of plunger 214, will allow fluid to move downward through tip reservoir portion 207 and exit through opening 215 of tip portion 205.

Figure 3A:
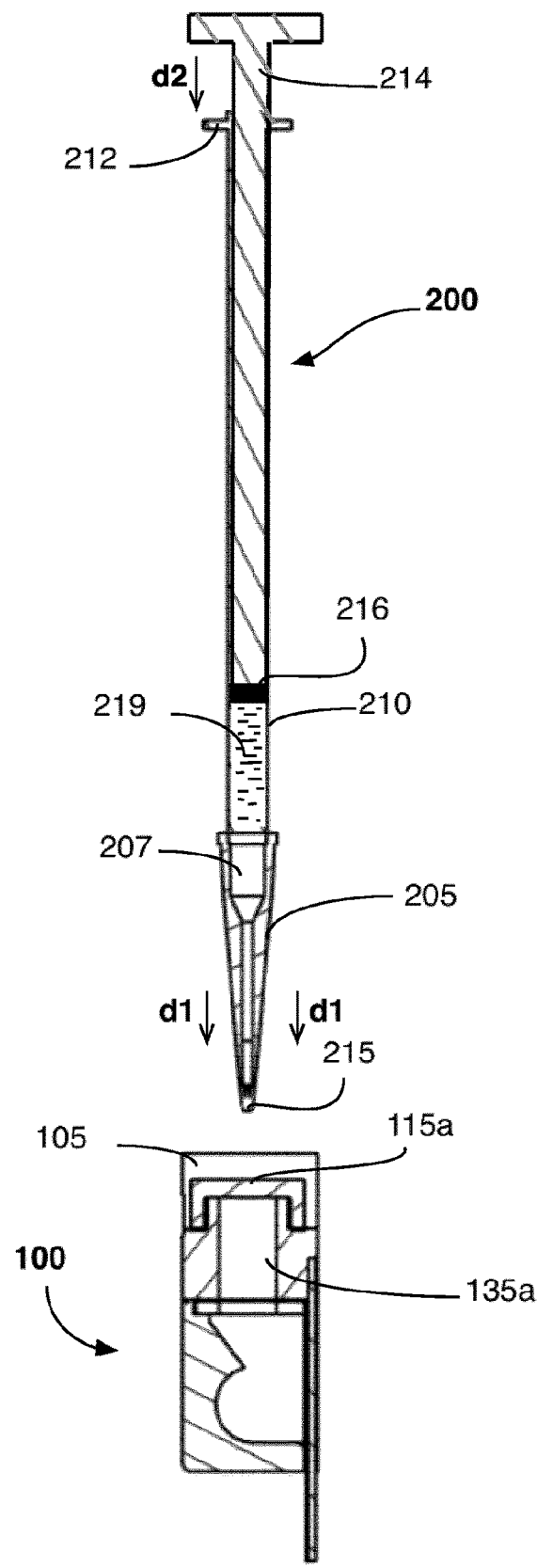
FIG. 3A is a vertical cross section view of the cartridge taken along the plane 1C in FIG. 1A, together with a fluid collection device, in a first state.
Figure 3B:
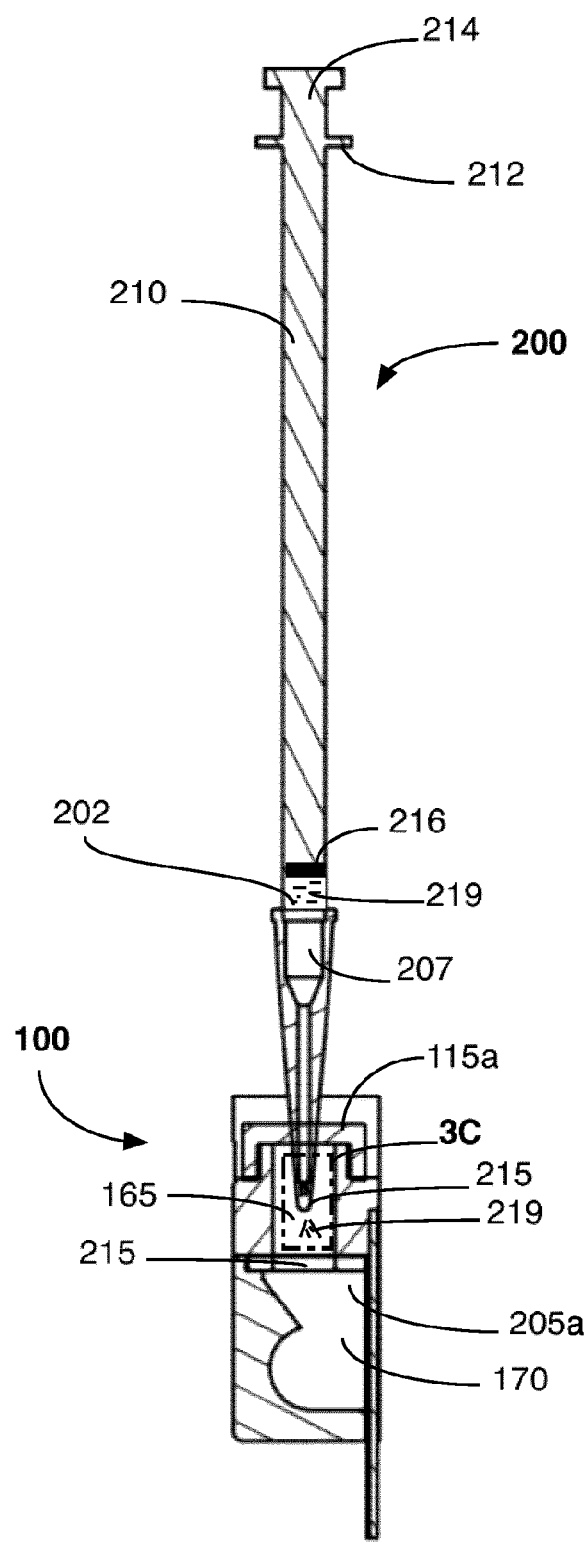
FIG. 3B is a vertical cross section view of the cartridge taken along the plane 1C in FIG. 1A, together with a fluid collection device, in a second state.
Figure 3C:
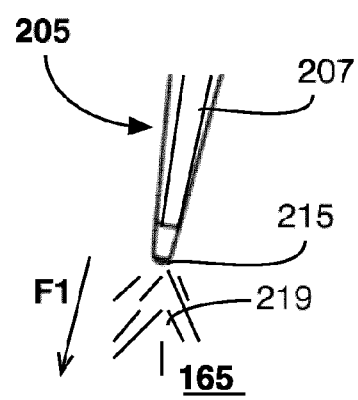
FIG. 3C is an enlarged perspective view of the area marked 3C in FIG. 3B.
Figure 4C:
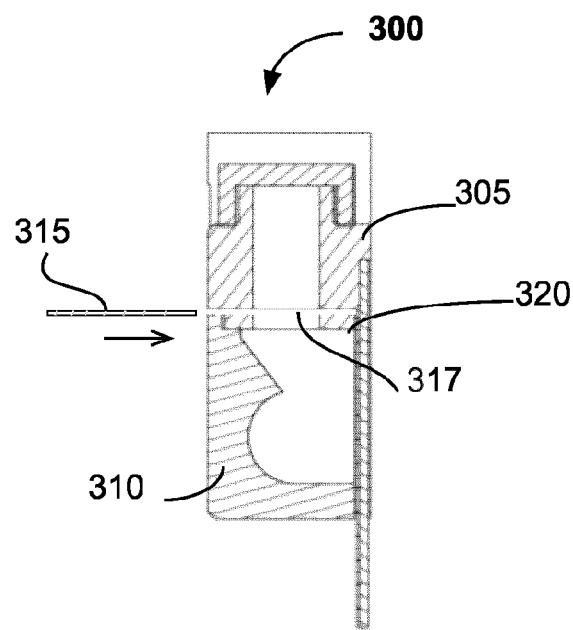
FIG. 4C is a cross section of a penetrable barrier.
Figure 4C:
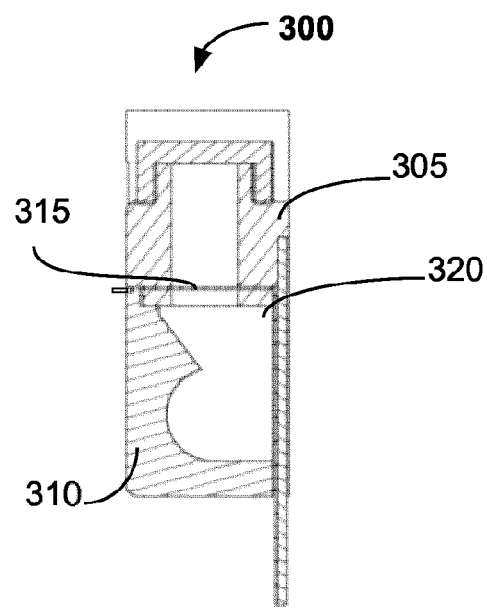
Figure 4C:
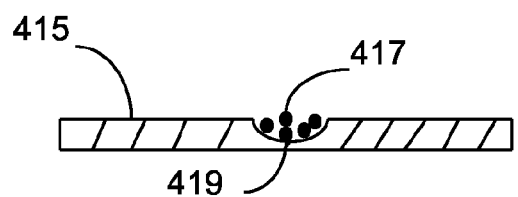

According to at least one example embodiment, cartridges of the present disclosure, such as example cartridge 100, can be operated in conjunction with fluid collection device 200, as shown in FIGS. 3A-3C.

Referring now to FIG. 3A, shown therein is example cartridge 100 and example fluid collection device 200 in a first state. There is no contact between cartridge 100 and fluid collection device 200. Fluid reservoir 210 of fluid collection device 200 contains fluid sample 219. Plunger 214, extending in downward direction to form piston 216, is in the shown first state extended in an upward position to thereby allow fluid sample 219 to be contained within fluid reservoir 210. Fluid collection device 200 can be moved in downward direction d1 towards penetrable barrier 115a of sample reservoir 135a within cartridge 100. Furthermore, downward direction d2 indicates downward movement of plunger fluid 214 within reservoir 210 of fluid collection device 200 after the tip of fluid collection device 200 has penetrated the barrier 115a.

Referring now to FIGS. 3B-3C, shown therein is example cartridge 100 and example fluid collection device 200 in a second state. Fluid collection device 200 has now engaged sufficiently forcefully with penetrable barrier 115a, to allow tip portion 205 to penetrate penetrable barrier 115a to extend into and be received by top compartment 165 of sample reservoir 135a. Furthermore after tip portion 205 of fluid collection device 200 has been placed into top compartment 165, plunger 214 is then moved downwards to result in release of fluid sample 219 into top compartment 165 of sample reservoir 135a. As can be seen better in FIG. 3C, fluid sample 219 is released from tip reservoir portion 207 into top compartment 165 (see: arrow F1). Contained in top compartment 165 is an activating compound, which can be provided, for example, as a dry particulate or liquid deposited on top surface of barrier 190. Thus, upon release of fluid sample 219 within top compartment 165, fluid sample 219 can contact the activating compound, and fluid parameters can cause the activation of the activating compound. Examples of activating compounds will hereinafter be described.

Figure 3D:
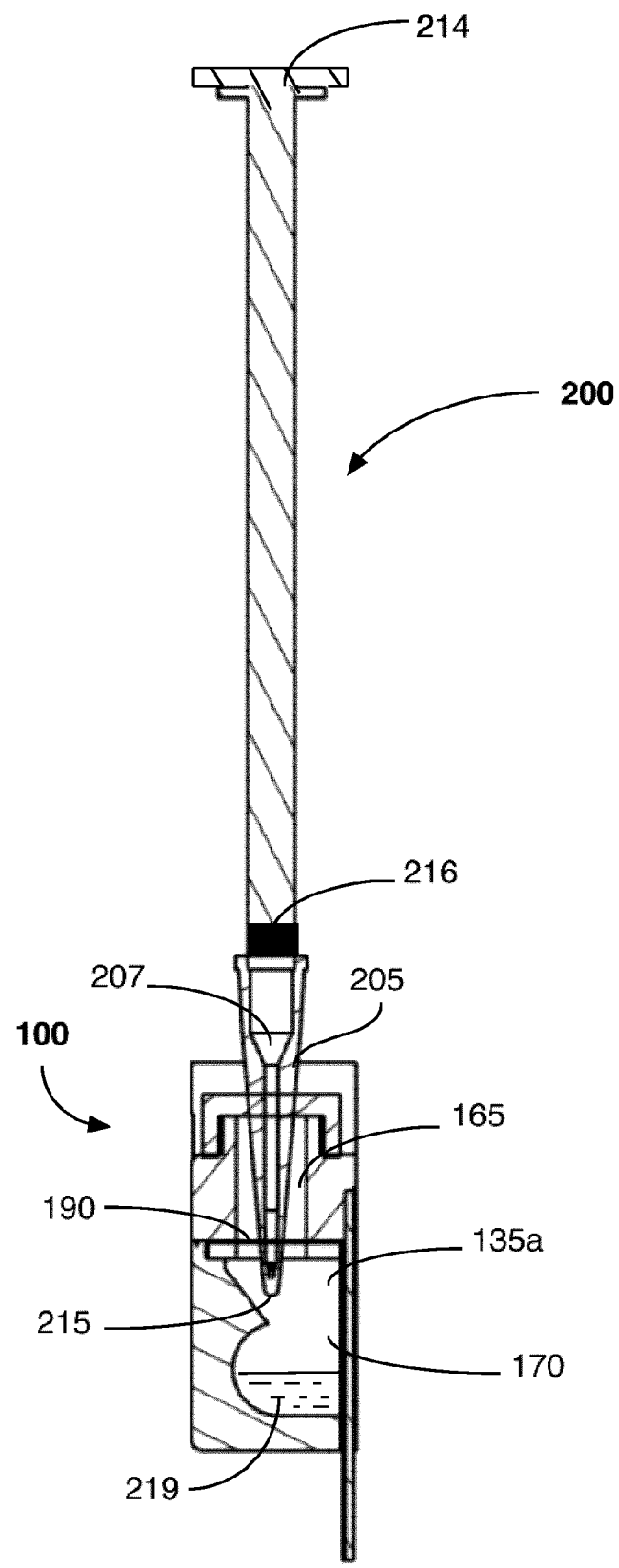
FIG. 3D is a vertical cross section view of the cartridge taken along the plane 1C in FIG. 1A, together with a fluid collection device, in a third state.

Referring to FIG. 3D, shown therein is example cartridge 100 and example fluid collection device 200 in a third state. Fluid collection device 200 has now engaged sufficiently forcefully with penetrable barrier 190, to allow tip portion 205 to penetrate penetrable barrier 190 and move further into the cartridge 100 to be received by bottom compartment 170 of sample reservoir 135a. Plunger 214 has been moved further downwards and a suitable amount, and possibly all, of fluid sample 219 has been released from fluid collection device 200. Penetration of penetrable barrier 190 has fluidically coupled top compartment 165 and bottom compartment 170. This has allowed the entry of fluid sample 219 from top compartment 165 of sample reservoir 135a into bottom compartment 170 thereof. Bottom compartment 170 contains an electroactive analyte, for example in the form of a liquid or a particulate, which has now been contacted by the activated compound to thereby activate the electroactive analyte.

It will be clear that in the foregoing example operational embodiment, fluid sample 219 can cause activation of the activating compound prior to fluidically coupling top compartment 165 and bottom compartment 170. In other operational embodiments, penetrable barriers 115a and 190 can both be penetrated prior to release of fluid sample 219 from fluid collection device 200, which in this case is not released in top compartment 165 of fluid reservoir 205a, but instead is released in bottom compartment 170 of sample reservoir 135a. In this operational embodiment, the sample fluid, the activating compound and the electroactive analyte can contact one another more or less simultaneously. It is noted that in such operational embodiments, the electroactive analyte can be placed in top compartment 165 and the activating compound can be placed in bottom compartment 170.

It is noted that penetrable barrier 190 is preferably fabricated using a tearable material, for example a foil or film, to facilitate fluidic coupling of top compartment 165 and bottom compartment 170 upon penetration thereof. By contrast, penetrable barrier 115a is preferably manufactured of a substantially non-tearable and/or sturdier material, but is a pierceable material, for example, such as rubber or silicone, so that following penetration of barrier 115a the possible influence of exterior parameters upon the reactions between fluid parameters and activating compound, and between activating compound and electroactive analyte, and the subsequent detection of the electroactive analyte, is limited because the pierceable material tightly surrounds tip portion 205. Alternatively, in another embodiment, penetrable barrier 190 can also be fabricated from a shatterable material, such as a shatterable plastic or glass. In yet other alternate embodiments, penetrable barrier 190 can, like penetrable barrier 115a, also be fabricated from a substantially non-tearable and/or sturdier material, but which is a pierceable material, such as rubber or silicone, for example, tightly surrounding tip portion 205.

It is further noted that in some embodiments, a penetrable barrier separating top and bottom compartments of the fluid analysis reservoir can be fabricated to include a portion shaped to contain the activating compound, for example, in this respect, one or more divots may be included within the penetrable barrier. An example of such penetrable barrier is shown in FIG. 4C. Shown therein is penetrable barrier 415 including divot 419 containing activating compound 417. Similarly, the bottom compartment 170, notably surface area 172 (see: FIG. 1C) can, in some embodiments, be fabricated to include divots to contain the electroactive analyte. In an alternative embodiment, divot 419 can contain the electroactive analyte and the bottom compartment 170, notably surface area 172, can be fabricated to include divots to contain the activating compound.

To briefly recap, a cartridge containing one or more sample analysis reservoirs has been provided. The sample analysis reservoir includes top and bottom compartments separated by the penetrable barrier 190 and can receive an end portion of a sample collection device containing a sample fluid. The sample collection device can release the fluid in either the top compartment 165 or, following penetration of the barrier 190, into the bottom compartment 170. The top and bottom compartments 165 and 170 contain an activating compound and an electroactive analyte, respectively, or an electroactive analyte and an activating compound, respectively. Upon release of the sample fluid in the sample reservoir 135a, 135b and/or 135c, the sample fluid, notably having a fluid parameter therein, can interact with the activating compound to thereby activate it, which in turn can activate the electroactive analyte. The activated electroactive analyte, in turn, can generate an electrical signal that is detected by the voltammetric sensors 125a, 125b and/or 125c allowing the presence of the fluid parameter to be detected when a voltage is applied to the voltammetric sensor across the sample analysis reservoir, as hereinafter further described.

Example embodiments of the fluid parameters, activating compounds and electroactive analytes will now be described.

Turning initially to the fluid parameter, it should be noted that the cartridge of the present disclosure can be used for the voltammetric detection of any fluid parameter, including any parameter relating to a physical property of a fluid i.e. a physical fluid parameter, such as fluid turbidity, temperature, density, or viscosity, for example, and any parameter relating to a chemical property of a fluid, i.e. a chemical fluid parameter, such as the presence of chemical substances in a fluid including, for example, organic molecules, biomolecules, or inorganic molecules. In one example embodiment, the fluid can be water, and the cartridge can be used to facilitate the testing of water quality, for example, by detecting the presence in a water sample of at least one toxic chemical substance; mineral ions including, but not limited, to magnesium ions, potassium ions, and carbonate ions, for example, as well as metallic ions including, but not limited, to iron ions, and lead ions, for example; as well as metalloid ions such as, but not limited, to arsenic ions, for example.

In another example embodiment, the fluid can be water, and the cartridge can be used to facilitate the testing of turbidity. In yet another example embodiment, the fluid can be water, and the cartridge can be used to facilitate testing of water quality, for example, by detecting the presence in the water sample of pollutants, for example, petroleum and petroleum derivatives, and toxins, for example, biologically-derived large polypeptide toxins, such as microcystin. The fluid parameter can vary, and it will readily be understood by those of skill in the art that in different embodiments the cartridges of the present disclosure can be used to detect a wide variety of fluid parameters in a wide variety of fluids, and that an activating compound and an electroactive analyte can be selected to detect a fluid and a fluid parameter, as desired. It is further noted that in embodiments hereof comprising two or more sample analysis reservoirs, each sample analysis reservoir may be used to detect the same fluid parameter, or different parameters, or may be provided with the same sample fluid or different sample fluids.

Turning now to the activation compound and the electroactive analyte, included, as herein before noted, these components are contained within a top or bottom compartment of an analysis reservoir of the cartridge, and in particular in such a manner that the top and bottom compartments 165 and 170, prior to use of the cartridge for voltammetric analysis, are fluidically separated. In general terms, activation compound and electroactive analyte can be selected such that a fluidic parameter of a sample fluid introduced in the fluid reservoir can activate the activating compound, and so that the activating compound, in turn, can activate the electroactive analyte, which can then be detected as a current by one of the voltammetric sensors 125a, 125b and 125c that corresponds to the sample/fluid analysis reservoir. In some embodiments, the top compartment 165 of the fluid reservoir can contain the activating compound and the bottom compartment 170 can contain the electroactive analyte. The activating compound upon release of the sample fluid in the top compartment 165 of the fluid reservoir will become activated. Subsequent penetration of the barrier 190 will result in activation of the electroactive analyte by the activated activating compound. In other embodiments, the top compartment 165 of the fluid reservoir can contain the electroactive analyte and the bottom compartment 170 can contain the activating compound. Only upon penetration of the barrier 190 by the sample fluid collection device, the sample fluid is expelled, the activating compound is contacted by the sample fluid to thereby become activated, and is in turn able to activate the electroactive analyte.

In some embodiments, the activating compound can be a compound which in prolonged contact with an electroactive analyte can cause sufficient activation of the electroactive analyte in the absence of a fluid parameter to detect a voltammetric electrical signal. Although these compounds are in principle suitable for voltammetric assays, they become unsuitable when kept together and in contact with one another for prolonged periods of time, for example, for more than one minute, an hour, a day, a week, a month, or a year or from about 10 minutes to about 120 minutes prior to use in a voltammetric assay. Prolonged contact between these activating compounds and the electroactive analytes can be said to spoil them for use in a voltammetric assay. It will be clear that the present cartridge is configured such that contact between the activating compound and electroactive analyte can be avoided until the performance of a voltammetric analysis, thereby preventing spoilage of these components. Accordingly, the cartridge and included activating compound and electroactive analyte can be stored for longer periods of time, for example for at least about one month, at least about six months or at least about 12 months.

In one embodiment, the activating compound can be an activating polypeptide such as but not limited to an enzyme, for example.

In one embodiment, the activating compound can be an activating polypeptide formed by cells contained in the top compartment 165, the cells comprising a promoter inducible by the fluid parameter and controlling the expression of the activating polypeptide. The cells can be living cells or dormant cells, for example, microbial spore cells. The cells can further be microbial cells, such as yeast cells or bacterial cells, *Escherichia* cells or *Bacillus* cells, for example, including, *Escherichia coli* cells, *Bacillus subtilis* cells and *Bacillus thuringiensis* cells.

In one embodiment, the cells can be dormant cells, and injection of fluid in the top compartment 165 causes the cells to exit dormancy and make an activating compound.

In one embodiment, the cells can be included in the top compartment 165 suspended in a liquid formulation, such as water or a buffer.

In one embodiment, the cells can be included in the top compartment 165 in a dry formulation or a substantially dry formulation, which can be prepared, by for example, freeze-drying (i.e. lyophilizing) or air-drying a liquid cell suspension.

In one embodiment, the cells can be included in the top compartment 165 in a gel formulation, in a gel matrix, for example.

In one embodiment, the cells can be microbial cells, and the activating polypeptide can be a hydrolase.

In one embodiment, the cells can be microbial cells, and the activating polypeptide can be a phosphatase.

In one embodiment, the cells can be microbial cells, and the activating polypeptide can be a selected from the group consisting of a β-galactosidase, β-glucuronidase and β-glucosidase.

The promoter inducible by the fluid parameter and controlling the expression of the activating polypeptide can be inducible promoters such as a copper sensitive promoter, including the cusR promoter ($P_{cusR}$), an iron sensitive promoter, including the fecA promoter ($P_{fecA}$), a lead sensitive promoter, including the pbrA promoter ($P_{pbrA}$), or an arsenic sensitive promoter including the arsR promoter ($P_{arsR}$). Further promoters that can be used are $P_{haA}$ (pH sensitive promoter), temperature sensitive promoters, including heat shock promoters (e.g. Hsp70 or Hsp90 promoters), light sensitive promoters (e.g. FixK2 promoter), or lac promoter (also known as $P_{lac}$) inducible by isopropyl-β-D-1-thiogalactopyranoside (IPTG).

In one embodiment, the electroactive analyte can be chlorophenol red-β-D-galactopyranoside (CPRG) and the activating compound can be β-galactosidase, such that upon contact between the electroactive analyte and the activating compound, chlorophenol red (CPR) is formed.

In one embodiment, the electroactive analyte can be para-nitrophenol-β-D-glucuronide (PNPG) and the activating compound can be β-glucuronidase, such that upon contact between the electroactive analyte and the activating compound, paranitrophenol (PNP) is formed.

In one embodiment, the electroactive analyte can be para-di-phenol-β-D-glucopyranoside (PDPG) and the activating compound can be β-glucosidase such that upon contact between the electroactive analyte and the activating compound, para-di-phenol (PDP) is formed.

In one embodiment, the electroactive analyte can be para-aminophenol-β-galactopyranoside (PAPG) and the activating compound can be β-galactosidase, such that upon contact between the electroactive analyte and the activating compound, para-aminophenol (PAP) is formed.

In one embodiment, the electroactive analyte can be para-aminophenyl phosphate (PAPP) and the activating compound can be a phosphatase, such that upon contact between the electroactive analyte and the activating compound, para-aminophenol (PAP) is formed.

In one example embodiment, the fluid parameter to be detected can be iron ions, the activating compound can be a formed by *Escherichia* cells (contained in a top compartment of a fluid analysis reservoir within a cartridge), the *Escherichia* cells comprising a fecA promoter inducible by iron ions and controlling the expression of β-galactosidase, which upon expression can activate para-aminophenol-β-galactopyranoside (contained in a bottom compartment 170 of a fluid analysis reservoir within a cartridge) to form the voltammetrically detectable compound para-aminophenol (PAP).

In one example embodiment, the fluid parameter to be detected can be xylene, the activating compound can be formed by *Bacillus thuringiensis* cells (contained in a top compartment 165 of a fluid analysis reservoir within a cartridge), for example, in the form of dry dormant *Bacillus thuringiensis* spores capable of exiting dormancy upon contact with fluid injected fluid in the top compartment, the *Bacillus thuringiensis* cells comprising a Pu promoter inducible by xylene and controlling the expression of β-glucosidase, which upon expression can activate para-di-phenol-β-D-glucopyranoside (contained in a bottom compartment of a fluid analysis reservoir within a cartridge) to form the voltammetrically detectable compound para-di-phenol (PDP).

It is noted that the foregoing represent example embodiments wherein the activating compound, by prolonged contact with an electroactive analyte, can cause sufficient activation of the electroactive analyte, even in the absence of a fluid parameter to detect a voltammetric electrical signal, i.e. small quantities of β-galactosidase can be produced even in the absence of the fluid parameter thus causing low levels of activation of the electroactive analyte. These low levels of β-galactosidase can be the result of the promoter, for example the fecA promoter or the ArsR promoter being 'leaky'. By separating the electroactive analyte from the activating compound, the cartridges of the present disclosure prevent activation of the electroactive analyte by, for example, β-galactosidase, as a result of a leaky promoter, prior to conducting the voltammetric assay.

Turning now to the assembly of the cartridges of the present disclosure during manufacturing, referring again to FIGS. 1A-C, in order to assemble cartridge 100 including the activating compound and the electroactive analyte, in one example embodiment, the following process may be followed. Top housing portion 105 and bottom housing portion 110 of cartridge 100 can be provided as separate components, together with appropriate quantities of the activating compound and electroactive analyte to be held within fluid reservoirs 135*a*, 135*b* and 135*c*. The electroactive analyte can readily be introduced, into bottom compartment 170 of each of the fluid reservoirs 135*a*, 135*b* and 135*c* of bottom housing portion 110, for example, by depositing a particulate electroactive analyte into bottom compartment 170. Thereafter, barrier 190 can be added and the activating compound can be introduced in top compartment 165 of each of the fluid reservoirs 135*a*, 135*b* and 135*c* of bottom housing portion 110, for example by depositing a particulate electroactive analyte into top compartment 165. It is noted that in different embodiments, the activating compound and electroactive analyte can be the same in each top compartment 165 and bottom compartment 170 of fluid reservoirs 135*a*, 135*b* and 135*c*, for example, to allow fluid samples obtained from multiple fluid sources to be evaluated using the same activating compound and electroactive analyte. In other embodiments, different activating compounds and electroactive analytes may be included in each top compartment 165 and bottom compartment 170 of fluid reservoirs 135*a*, 135*b* and 135*c*, for example, to allow a fluid sample obtained from the same fluid source to be evaluated voltammetrically with respect to different fluid parameters. Finally, top housing portion 105 can be slidably mounted on bottom housing portion 110.

In at least one embodiment, cartridges can be constructed to include a releasable penetrable barrier. An embodiment of an example cartridge 300 is shown in FIGS. 4A and 4B. As can be seen, sample analysis reservoir 320 comprises slot 317 between the first and second compartments to slidably receive penetrable barrier 315 in order to separate top compartment 305 from bottom compartment 310. Barrier 315 can be releasably inserted and removed from slot 317 of cartridge 310.

This embodiment permits the introduction of the activating compound, or the electroactive analyte following assembly of top and bottom housing compartments 305 and 310. In this embodiment the penetrable barrier 315 can optionally contain one or more divots, such as shown in FIG. 4C.

According to one example embodiment, cartridges of the present disclosure, such as example cartridges 100 and 300, can be operated in conjunction with voltammetric detection device 500, as shown in FIGS. 5A-5C.

The cartridges of the present disclosure can be inserted into a voltammetric detection device. In general, the voltammetric detection device is electronically configured to be able to receive a cartridge of the present disclosure and to apply a voltage to the voltammetric sensors of the cartridge. The voltammetric detection device is further generally electronically configured to detect the current passing through the sensor upon the application of the voltage to the sensor.

Voltammetric techniques, methodologies and devices are generally known to those of skill in the art. In what follows, some example techniques and devices are described in general terms. It will be clear to those of skill in the art that voltammetric detection devices and techniques used in conjunction with the cartridges of the present disclosure may be varied and adjusted.

Referring to FIG. 6, shown therein is a flowchart showing an example embodiment of method 600 for voltammetric detection of a fluid parameter in a fluid sample, in accordance with the teachings herein. Method 600 refers to the cartridge of FIGS. 1A-D and the fluid collection device of FIGS. 2A-C for ease of illustration but method 600 can be applied to alternative embodiments of the cartridges and fluid collection devices. At act 602 of method 600, a fluid sample is collected from a source fluid in fluid collection device 200. At act 604 of method 600, the end portion 205 of fluid collection device 200 is sufficiently forcefully engaged with penetrable barrier 115*a* to penetrate penetrable barrier 115*a*, and to be received by fluid reservoir 135*a*, notably by top compartment 165. At this time, in some embodiments, cartridge 100 can be uncoupled from a voltammetric detection device. In other embodiments, cartridge 100 can be coupled to a voltammetric detection device, for example, by insertion in a slot of a voltammetric detection device, the slot being configured to permit the releasable insertion of cartridge 100 therein. At act 606 of method 600, the sample fluid is released from fluid collection device 200 into fluid reservoir 135a. In at least one embodiment, sample fluid is released from fluid collection device 200 in top compartment 165, and thereafter end portion 205 engages with sufficient force with penetrable barrier 190 to penetrate penetrable barrier 190 to fluidically connect top compartment 165 and bottom compartment 170. In at least one embodiment, end portion 205 can engage with sufficient force with penetrable barrier 190 to penetrate penetrable barrier 190 to fluidically connect top compartment 165 and bottom compartment 170, and thereafter sample fluid can be released from fluid collection device 200. Release of sample fluid from fluid collection device 200 causes a fluid parameter in the sample to activate an activating compound contained in top compartment 165, and subsequently the activated activating compound then activates an electroactive analyte contained in bottom compartment 170. In some embodiments, mixing of the sample fluid, activating compound and electroactive analyte may be further be facilitated by shaking cartridge 100. At act 608 of method 600 a voltage is applied to voltammetric sensor cartridge 100 after the cartridge 100 has been coupled to a voltage source. At act 610 of method 600 current is detected, cartridge 100 having also been coupled to a current detector prior to application of the voltage. In at least one embodiment voltage source and current detector can be included in one voltammetric detection device. As hereinbefore described, in alternate embodiments, bottom compartment 170 can contain the activating compound, and top compartment 165 can contain the electroactive analyte.

Turning now to the voltammetric detection device, a wide variety of voltammetric detection devices and voltammetric detection techniques can be used in accordance with the teachings hereof. Referring to FIG. 7, shown therein is an example block diagram for a configuration of a suitable voltammetric detection device 700 comprising housing 714 and output element 704, coupled to voltammetric sensor 706. Voltage source 708 is coupled to voltammetric sensor 706 and to controller 702 which can control voltammetric sensor 706 to apply a voltage to voltammetric sensor 706. When voltammetric sensor 706 is in contact with an electroactive analyte, for example, when a fluid sample is introduced in a cartridge including voltammetric sensor 706, as hereinbefore described, a voltage is applied to the cartridge which causes an electric current (i.e. electrical signal) to pass through voltammetric sensor 706 and be detected by current detector 710 while the applied voltage can be detected by voltage detector 712. Current detector 710 and voltage detector 712 are also connected to controller 702. Controller 702 can provide measurements of the detected electrical currents and applied voltage to output element 704. In example embodiment 700 shown in FIG. 7, voltage source 708, current detector 710, voltage detector 712 and controller 702 are contained in housing 714. Output element 704 coupled to controller 702 is not contained in housing 714, and may, for example, be wirelessly coupled to controller 702, via, for example, a cellular, Bluetooth® or wifi communication protocol. In other embodiments, output element 704 can also be contained in housing 714. Output element 704 may be a display, for example, a liquid crystal display (LCD) or a light emitting diode (LED) display, or be provided in the form a series of indicator LED lights, e.g. green, orange, red to indicate low, medium and high levels of a liquid parameter. Controller 702 includes a processor and/or detection circuitry and may process the detected electrical current and applied voltage to perform a measurement of the fluid parameter which may then be shown by the output element 704. In detecting or measuring the fluid parameter, the detected current can be compared to a threshold to ascertain the presence the fluid parameter in the fluid sample. Controller 702 may be further be coupled to a memory device or include a memory element (both not shown) in order to store one or more of the measured detected electrical current, the measured detected applied voltage and the measured fluid parameter. The memory device may be removably coupled to housing 714, for example, via a Universal Serial Bus (USB) connection. It will be clear to those of skill in the art that various housing configurations can be assembled, including multiple housings separately or jointly containing a controller, an output element, a voltage source, a current detector, a voltage detector, and a memory device.

Thus, by way of one example, a water sample suspected to contain a certain amount of arsenic can be collected by a fluid collection device and then introduced by the fluid collection device in a cartridge of the present disclosure, as herein described. The cartridge can contain cells comprising p-galactosidase controlled by arsR promoter ($P_{arsR}$) in the top compartment 165 of a given sample reservoir. In the bottom compartment 170 of the given sample reservoir the electroactive analyte aminophenol-β-galactopyranoside (PAPG) can be included. Upon the water sample contacting the cells, in the presence of arsenic in the water sample, β-galactosidase can be produced, and upon penetration of the barrier between the top and bottom compartments 165 and 170, the electroactive analyte can be activated by β-galactosidase to form para-aminophenol (PAP), which can contact voltammetric sensor 706. Upon placement of the cartridge in a voltammetric detection device, a voltage can be applied by voltage source 708 to voltammetric sensor 706 using controller 702 and the applied voltage can cause an electric current to pass through voltammetric sensor 706. The flow of the electrical current can then be detected by current detector 710, and the applied voltage can be detected by voltage detector 712. Controller 702 can provide measurements of the detected current and applied voltage to output element 704 for evaluation by an operator of the voltammetric detection device. A control cartridge, for example a cartridge containing a water sample known to not contain arsenic, can be used to compare and/or quantitate the detected current relative to the current detected in the water sample suspected to contain arsenic to determine if the detected current exceeds a threshold. In instances in which the detected current exceeds the threshold represented by a control, arsenic can be said to be present in the water sample. The controller 702 can be programmed to perform the comparison with the threshold and output the result to output element 704.

The voltammetric detection device can be a device operable such that a voltage can be applied to the cartridge potentiostatically (i.e. at one voltage), incrementally at different selected voltages, e.g. in square-wave voltammetric fashion, or in a cyclical voltammetrical fashion (i.e. scanned linearly across a range of defined voltages). Further included are devices operable based on any voltamperometric methodology, including, without limitation, pulse voltammetry, linear sweep voltammetry, square-wave voltammetry, chronoamperometry, staircase voltammetry, and cyclical voltammetry, and variations or adaptations thereof such as differential pulse voltammetry, or wave based voltammetry with chronoamperometric steps included in the sweeps. In general, in accordance herewith, the application of voltage to the sample fluid can results in the oxidation or reduction of the electroactive analyte and gain or release of electrons by the electroactive analyte or voltammetric sensor, which can be measured amperometrically in the form of a current.

The voltammetric sensor generally can comprise one or more working electrode components, a reference electrode component, and a counter electrode component. The reference electrode can be any electrode that holds a consistent voltage, and may be a suitable Ag/AgCl, saturated calomel electrode (SCE), or a saturated sodium chloride calomel electrode (SSCE). The counter electrode may, for example, be a gold electrode, a platinum electrode, or a carbon electrode, e.g. a printed carbon, glassy carbon or Vulcan carbon electrode. Gold or glassy carbon electrodes may be less suitable for use in disposable cartridges in view of the manufacturing cost. The working electrode may vary in composition, and, can for example, be a gold, platinum or carbon electrode, or a nanotube or nanoparticle electrode, or a graphene electrode. Examples of preferred combinations of electrodes include: 1) a gold working electrode, a reduction of hydrogen reference electrode, and a platinum counter electrode; 2) a glassy carbon working electrode, a carbon counter electrode, and an Ag/AgCl reference electrode; 3) a platinum working electrode, a gold counter electrode, and an SCE reference electrode; and 4) a carbon working electrode, a carbon counter electrode, and an Ag/AgCl reference electrode. In general, glassy carbon working electrodes may be selected for initial exploratory work in view of their general stability. Carbon working electrodes and counter electrodes and Ag/AgCl reference electrodes may be more preferable for use in the manufacture of disposable cartridges in view of the more limited manufacturing cost of these electrodes. It is further possible to coat electrodes e.g. by thiolate self-assembled monolayers on a metal surface (e.g. gold), and/or protected. For example, a carbon electrode may be protected by applying phthalocyanine layer, by application of certain ions or metals, e.g. nickel, which may be dried on the electrode surface or by platinum which may be plated on the surface. Combinations of the foregoing may also be applied. In at least one embodiment, screen printed electrodes may be used, for example, using a ceramic or plastic printing substrate, and paste electrodes, for example, a carbon paste for the working and counter electrodes, and an Ag/AgCl paste as a reference electrode.

Voltages may be applied to a fluid using any stable reference electrode, including, without limitation, an Ag/AgCl, saturated calomel electrode (SCE), a saturated sodium chloride calomel electrode (SSCE), or a reduction of hydrogen electrode (RHE), and the amplitude of the voltage that is applied can be selected between a first value that results in the production of oxygen from water at the positive end of the spectrum, and a second value that results in the production of hydrogen from water at the negative end of the spectrum and can depend on the particular electrodes that are used. For example, voltages can be applied in the range from 0-2.0 V versus an RHE reference electrode, or −1 Volt to +1 Volt against a pseudo Ag/AgCl reference electrode. Amperages detected can range, for example, from 1 nA to 1 mA, or more, when a potentiostatic voltage is applied, or from about 10 nA to 100 µA, or more when using cyclic voltammetry.

Flow of an electrical current and detection thereof, upon application of a voltage to the sample fluid in the cartridge signals the presence of a fluid parameter in the assay sample. Conversely, the absence of an electrical signal or the detection of an electrical signal below a threshold value, upon the application of a voltage to the assay medium, is indicative of the absence of the fluid parameter in the fluid sample. In this manner, the detection of the electrical signal, in accordance with the present disclosure, correlates with the presence of the fluid parameter in the fluid. Flow of an electrical current can be evaluated and/or quantitated by the controller 702 and then output using a display device as the output element 704, for example a digital display device, electronically configured to display the measured flow of an electrical current that is detected. The display device can be included in the voltammetric detection device, or it can be separately couplable thereto. In at least one embodiment, the voltammetric detection device can further include an electronic memory component to store the data associated with the measured detected electrical currents, measured detected applied voltages and the measured fluid parameter(s).

Figure 8A:
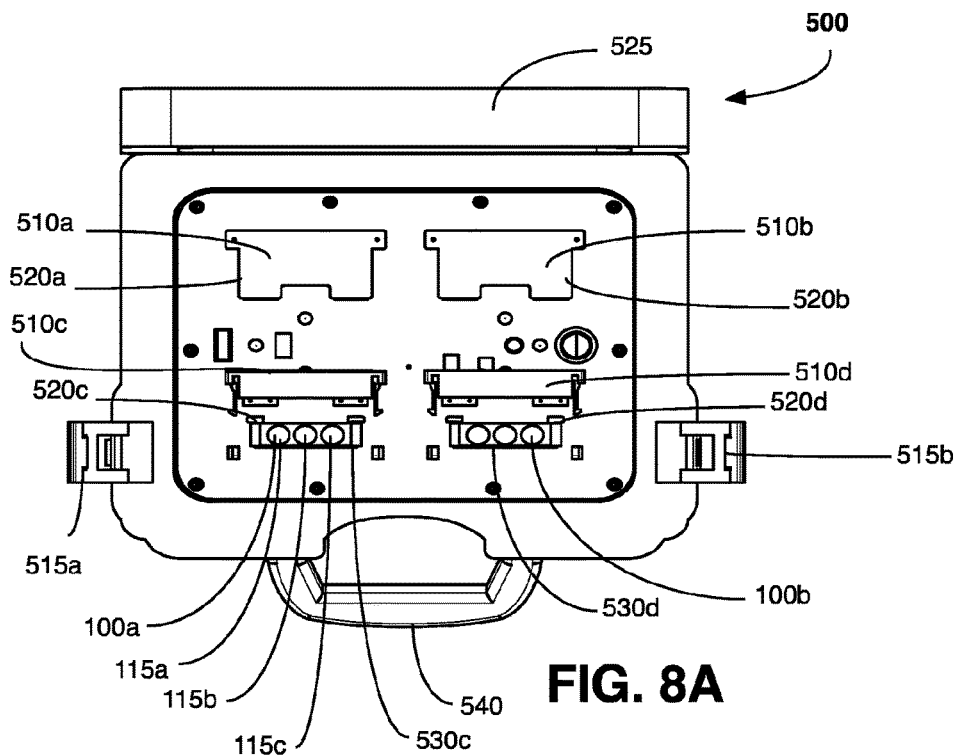
FIG. 8A is a top view of a voltammetric detection device with two cartridges inserted in cartridge holders, showing the two cartridge holders in an open position, and two cartridge holders in a closed position, and the voltammetric detection device in an open position.
Figure 8B:
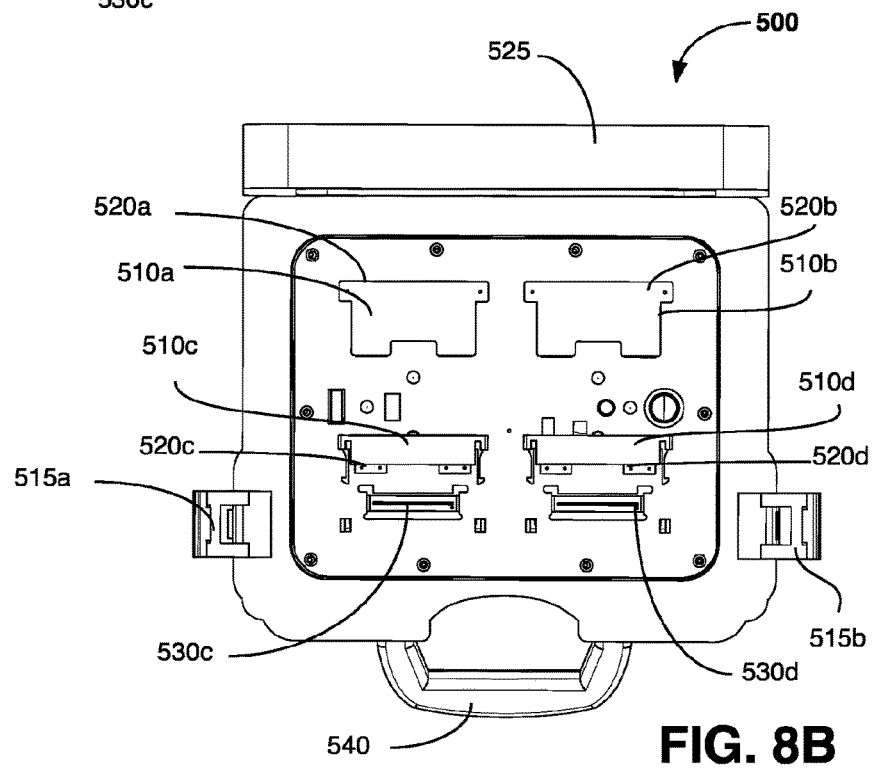
FIG. 8B is a top view of a voltammetric detection device showing the two cartridge holders in an open position without cartridges inserted, and two cartridge holders in a closed position, and the voltammetric detection device in an open position.

Referring now FIGS. 5A-C and FIGS. 8A-B, shown therein is an example handheld voltammetric detection device 500. Voltammetric detection device 500 includes container 520 having openable lid 525. Handgrip 540 allows for convenient transportation of voltammetric detection device 500, for example to a location in close proximity of a fluid sampling site. Lid 525 can be securely closed by clips 515a and 515b. Detection device 500 further includes four cartridge holders 520a, 520b, 520c and 520d comprising slots that are each capable of releasably receiving different cartridges. Shown in this respect in FIG. 8B are slots 530c and 530d without a cartridge received therein, and in FIG. 8A, slots 530c and 530d with cartridge 100a and 100b, respectively, received therein. Each slot can further be covered by hingeable cartridge lid 510a, 510b, 510c and 510d. In FIG. 8A and FIG. 8B, hingeable cartridge lids 510c and 510d are shown in a hinged open position. It is noted that two slots, in addition to slots 530c and 530d, are not visible in FIG. 8A and FIG. 8B since these slots are covered by hingeable cartridge lids 510a and 510b. Similarly, in FIG. 5A, only slot 530d, having cartridge 100b inserted therein, is visible, the other three slots being covered by hingeable cartridge lids 510a, 510b and 510c. Voltammetric device 500 further includes the electronic circuitry required for performing voltammetric detection using cartridge 100, and this electronic circuitry can, for example, be configured as shown in FIG. 7. In different embodiments, the voltammetric detection device can comprise two, three, four, five or six insertion slots. For example, the slots may be configured to be identical or they may be configured differently, e.g. each slot may be configured to be able to receive the same cartridges, or different cartridges, e.g. cartridges having different voltammetric sensors. Voltammetric detection device 500 can be used for the voltammetric detection of a fluid parameter present in a fluid sample introduced in cartridge 100 inserted in one of slots 530a, 530b, 530c and 530d of voltammetric detection device 500.

It is noted that in some embodiments, slots 530a, 530b, 530c and 530d and/or cartridges (e.g. 100a and 100b) can be color coded. Similarly, penetrable barriers, e.g. 115a, 115b and 115c of cartridge 100a can be color coded. Such color coding can facilitate the analysis of different fluid parameters in different fluid reservoirs or cartridges. Thus, for example, each cartridge can include three different colored penetrable barriers, indicating intended use for the detection of three different chemical substances in each of the three reservoirs; or each of the four slots can be color coded and pairing with a similarly color coded cartridge, indicating intended use of the cartridge/slot for the detection of four different chemical substances.

As can now be appreciated, the cartridges of the present disclosure can be used for the voltammetric detection of fluid parameters in fluid samples. The cartridges can be used to detect fluid parameters, for example, in a water sample, directly at the site at which the sample is acquired in order to thereby evaluate water quality.

Of course, the above described example embodiments of the present disclosure are intended to be illustrative only and in no way limiting. The described embodiments are susceptible to many modifications of composition, details and order of operation. The invention, rather, is intended to encompass all such modifications within its scope, as defined by the claims, which should be given a broad interpretation consistent with the description as a whole.

EXAMPLES

Hereinafter are provided examples of further specific embodiments for performing the methods of the present disclosure, as well as embodiments representing the devices of the present disclosure. It is noted that the examples are provided in further reference to using the devices shown in FIGS. 1-8 and the results are shown in FIGS. 9-18.

Example 1—Cyclic Voltammetry Using β-galactosidase to Produce PAP as an Electroactive Analyte A cartridge 100 was constructed to include a voltammetric sensor 706 comprising a working carbon electrode, a working carbon counter electrode and an Ag/AgCl reference electrode. Cartridge 100 was then prepared to contain 0.16 ml of a 5 mM para-aminophenol-β-galactopyranoside (PAPG) solution in 0.2M pH 7 sodium phosphate buffer in a bottom compartment 170 of sample reservoirs 135a and 135b of cartridge 100. The solution was left to evaporate and form a crystalline residue. A total of 1 unit β-galactosidase was introduced into the top compartment 165 of sample reservoir 135a of cartridge 100. No β-galactosidase was introduced into the top compartment 165 of sample reservoir 135b of cartridge 100. Using a fluid collection device, substantially similar to fluid collection device 200, 800 µL of water was introduced into each of two bottom compartments 170 of sample reservoirs 135a and 135b of cartridge 100 following piercing of each penetrable barrier 190. Cartridge 100 was then briefly shaken to ensure mixing of the β-galactosidase, water, and PAPG, and the mixture was left to incubate, to thereby allow for degradation of PAPG by β-galactosidase to form para-aminophenol (PAP). Thereafter, cartridge 100 was operably placed in a cartridge holder 520a of a voltammetric detection device 500 and a voltage was applied in a cyclical voltammetric fashion at 50 mV/s from −0.4 V to +0.4 V across a carbon counter electrode versus an Ag/AgCl reference electrode, and measurements were made using a carbon working electrode with respect to the reference electrode. A voltammetric graph was prepared for the sample in each of the sample reservoirs 135a and 135b, as shown in FIG. 9. It is noted that no change in current was detected as a function of a change in the cyclically applied voltage in sample reservoir 135b, not containing any β-galactosidase. By contrast, in sample reservoir 135a, a change in current was detected as a function of a change in the applied voltage. The change in current can be interpreted to be caused by the presence in sample reservoir 135a of electroactive analyte PAP, formed by the enzymatically catalyzed degradation of PAPG by the enzyme β-galactosidase.

Example 2—Cyclic Voltammetry Using Protein Phosphatase 1 (PP1) to Produce PAP as an Electroactive Analyte A cartridge 100 was constructed to include a voltammetric sensor 706 comprising a working carbon electrode, a working carbon counter electrode and a Ag/AgCl reference electrode. Cartridge 100 was then prepared to contain 0.16 ml of a 5 mM para-aminophenyl phosphate (PAPP) solution in 0.2M pH 7 sodium phosphate buffer in a bottom compartment 170 of sample reservoirs 135a and 135b of cartridge 100. The solution was left to evaporate and form a crystalline residue. A total of 1 µg protein phosphatase 1 (PP1) was introduced into the top compartment 165 of sample reservoir 135a of cartridge 100. No PP1 was introduced into the top compartment 165 of sample reservoir 135b of cartridge 100. Using a fluid collection device, substantially similar to fluid collection device 200, 800 µL water was introduced into each of two bottom compartments 170 of sample reservoirs 135a and 135b of cartridge 100 following piercing of each penetrable barrier 190. Cartridge 100 was then briefly shaken to ensure mixing of the PP1, water, and PAPP, and the mixture was left to incubate, to thereby allow degradation of PAPP by PP1 to form PAP. Thereafter, cartridge 100 was operably placed in a cartridge holder 520a of a voltammetric detection device 500, and a voltage was applied in a cyclical voltammetric fashion at 50 mV/s from −0.4 V to +0.4 V across a carbon counter electrode versus an Ag/AgCl reference electrode, and measurements were made using a carbon working electrode with respect to the reference electrode. A voltammetric graph was prepared for the sample in each of the sample reservoirs 135a and 135b, as shown in FIG. 10 It is noted that no change in current was detected as a function of a change in the cyclically applied voltage in sample reservoir 135b, not containing any PP1. By contrast, in sample reservoir 135a, a change in current was detected as a function of a change in the applied voltage. The change in current can be interpreted to be caused by the presence in sample reservoir 135a of electroactive analyte PAP, formed by the enzymatically catalyzed degradation of PAPP by the enzyme PP1.

Example 3—Evaluation of Voltammetric Reaction Time of Bacterial Cells Expressing β-galactosidase to Produce PAP as an Electroactive Analyte in a Single Compartment Sample Analysis Reservoir An alternative cartridge including a sample analysis reservoir comprising a single compartment and no penetrable barrier was constructed. The alternative cartridge further included a voltammetric sensor comprising a working carbon electrode, a working carbon counter electrode and a Ag/AgCl reference electrode. The cartridge was then prepared to contain 0.16 ml of a 5 mM para-aminophenol-β-galactopyranoside (PAPG) solution in 0.2 M pH 7 sodium phosphate buffer in the single compartment of the sample analysis reservoir of the cartridge. The solution was left to evaporate and form a crystalline residue. Using a fluid collection device, substantially similar to fluid collection device 200, a total volume of 200 µL of a liquid culture of *Escherichia coil* containing an As(III)-inducible β-galactosidase expression plasmid was introduced into the sample analysis reservoir. The cartridge was then briefly shaken to ensure mixing of the *E. coli* culture and PAPG and the mixture was left to incubate. Thereafter, the cartridge was operably placed in a cartridge holder of a voltammetric detection device, and a voltage was applied in a cyclical voltammetric fashion at 50 mV/s from −0.4 V to +0.4 V across a carbon counter electrode versus an Ag/AgCl reference electrode, and measurements were made using a carbon working electrode with respect to the reference electrode. The maximum value of the voltammetric current (associated with the presence of para-aminophenol (PAP), the product of enzymatic degradation of PAPG) detected was recorded at different incubation time points (t=0; t=10 mins; t=20 mins; t=30 mins; t=40 mins t=50 mins and t=60 mins). A bar graph of the results is shown in FIG. 11. These results illustrate that even in the absence of an inducing agent (i.e. As(III)), β-galactosidase when in contact for a period of time with PAPG exhibits catalytic activity resulting in the enzymatic degradation of PAPG and the formation of voltammetrically detectable quantities of PAP.

Figure 12:
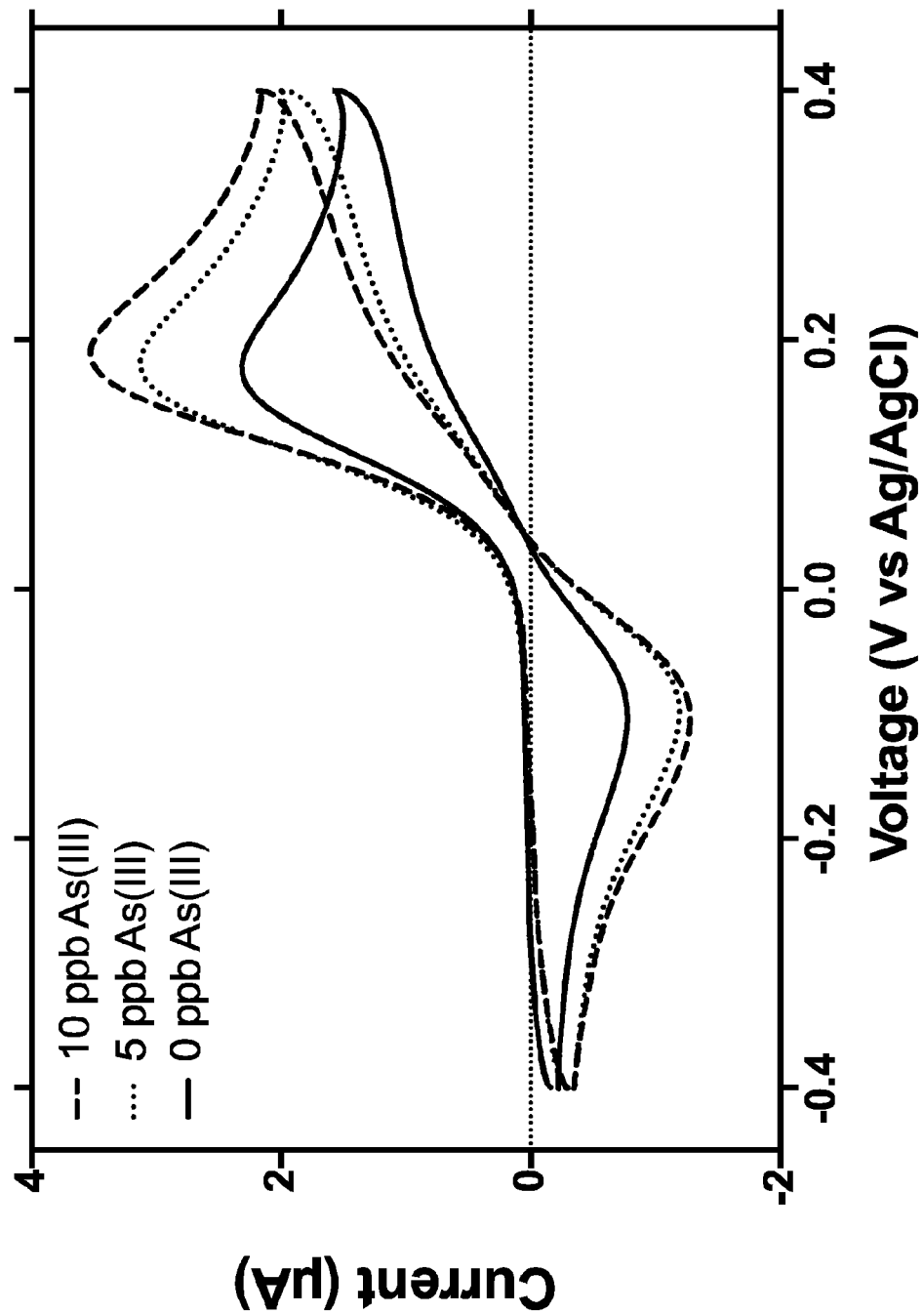
FIGS. 12 to 17 are voltammetry graphs illustrating experimental results obtained using example embodiments of a cartridge and a voltammetric detection device of the present disclosure.

Example 4—Cyclic Voltammetric Detection of Arsenite in a Water Sample Using Bacterially Expressed β-galactosidase Controlled by an Arsenite Inducible Promoter and Using PAP as an Electroactive Analyte A cartridge 100 was constructed to include a voltammetric sensor 706 comprising a working carbon electrode, a working carbon counter electrode and a Ag/AgCl reference electrode. Cartridge 100 was then prepared to contain 0.16 ml of a 5 mM para-aminophenol-β-galactopyranoside (PAPG) solution in 0.2M pH 7 sodium phosphate buffer in each of the bottom compartments 170 of sample reservoirs 135*a*, 135*b* and 135*c* of cartridge 100. The solution was left to evaporate and form a crystalline residue. A total volume of 200 μL of a liquid culture of *Escherichia coli* containing an As(III)-inducible β-galactosidase expression plasmid was introduced into each of the top compartments 165 of sample reservoirs 135*a*, 135*b* and 135*c* of cartridge 100. Using a fluid collection device, substantially similar to fluid collection device 200, three 800 μL water samples containing 0 parts per billion (ppb), 5 ppb, or 10 ppb As (III), respectively, were introduced into each bottom compartment 170 of sample reservoirs 135*a*, 135*b* and 135*c* of cartridge 100 following piercing of each penetrable barrier 190. Cartridge 100 was then briefly shaken to ensure mixing of the *E. coli* culture, the water samples, and PAPG, and the mixture was left to incubate, to thereby allow for induction of β-galactosidase expression by As(III) and degradation of PAPG to form para-aminophenol (PAP). Thereafter, cartridge 100 was operably placed in a cartridge holder 520*a* of a voltammetric detection device 500, and a voltage was applied in a cyclical voltammetric fashion at 50 mV/s from −0.4 V to +0.4 V across a carbon counter electrode versus an Ag/AgCl reference electrode, and measurements were made using a carbon working electrode with respect to the reference electrode. Voltammetric graphs were prepared for each sample and are shown in FIG. 12. It is noted that the maximum value of the voltammetric current obtained using the water sample containing 10 ppb of As(III) exceeds the maximum value of the voltammetric current obtained using the water sample containing 5 ppb of As(III), which, in turn, exceeds the maximum value of the voltammetric current obtained using the water sample containing C ppb of As(III).

Figure 13:
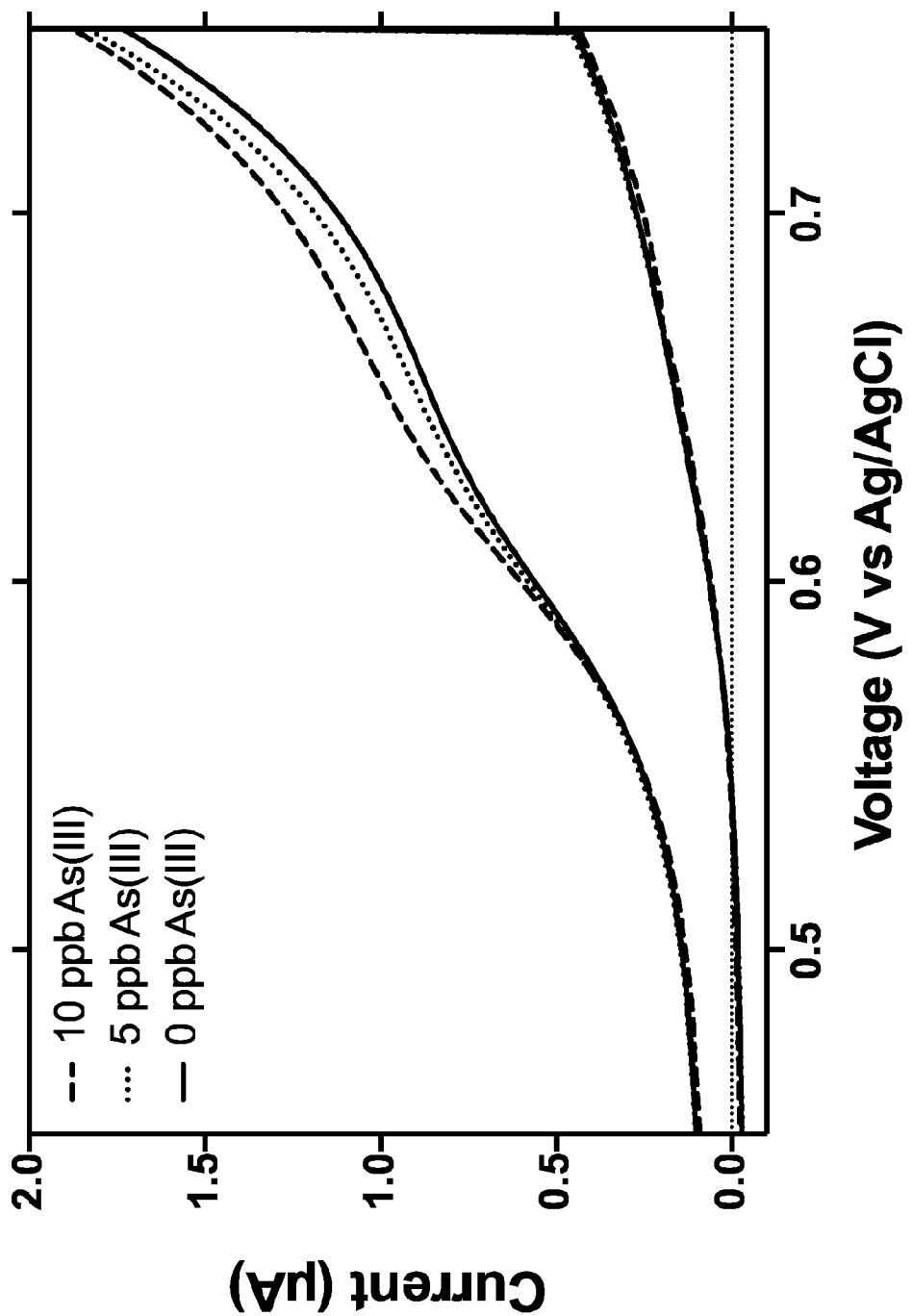

Example 5—Cyclic Voltammetric Detection of Arsenite in a Water Sample Using Bacterially Expressed β-galactosidase Controlled by an Arsenite Inducible Promoter and Using CPR as an Electroactive Analyte A cartridge 100 was constructed to include a voltammetric sensor 706 comprising a working carbon electrode, a working carbon counter electrode and a Ag/AgCl reference electrode. Cartridge 100 was then prepared to contain 0.16 ml of a 5 mM chlorophenol red-β-D-galactopyranoside (CPRG) solution in 0.2M pH 7 sodium phosphate buffer in each of the bottom compartments 170 of sample reservoirs 135*a*, 135*b* and 135*c* of cartridge 100. The solution was left to evaporate and form a crystalline residue. A total volume of 200 μL of a liquid culture of *Escherichia coli* containing an As(III)-inducible β-galactosidase expression plasmid was introduced into each of the top compartments 165 of sample reservoirs 135*a*, 135*b* and 135*c* of cartridge 100. Using a fluid collection device, substantially similar to fluid collection device 200, three 800 μL water samples containing 0 parts per billion (ppb), 5 ppb, or 10 ppb As (III), respectively, were introduced into each bottom compartment 170 of sample reservoirs 135*a*, 135*b* and 135*c* of cartridge 100 following piercing of each penetrable barrier 190. Cartridge 100 was then briefly shaken to ensure mixing of the *E. coli* culture, and the water samples and CPRG and the mixture was then left to incubate, to thereby allow for induction of β-galactosidase expression by As(III) and degradation of CPRG to form chlorophenol red (CPR). Thereafter, cartridge 100 was operably placed in a cartridge holder 520*a* of a voltammetric detection device 500, and a voltage was applied in a cyclical voltammetric fashion at 50 mV/s from 0 V to +1 V across a carbon counter electrode versus an Ag/AgCl reference electrode, and measurements were made using a carbon working electrode with respect to the reference electrode. Voltammetric graphs were prepared for each sample and are shown in FIG. 13. It is noted that the maximum value of the voltammetric current obtained using the water sample containing 10 ppb of As(III) exceeds the maximum value of the voltammetric current obtained using the water sample containing 5 ppb of As(III), which, in turn, exceeds the maximum value of the voltammetric current obtained using the water sample containing 0 ppb of As(III).

Figure 14:
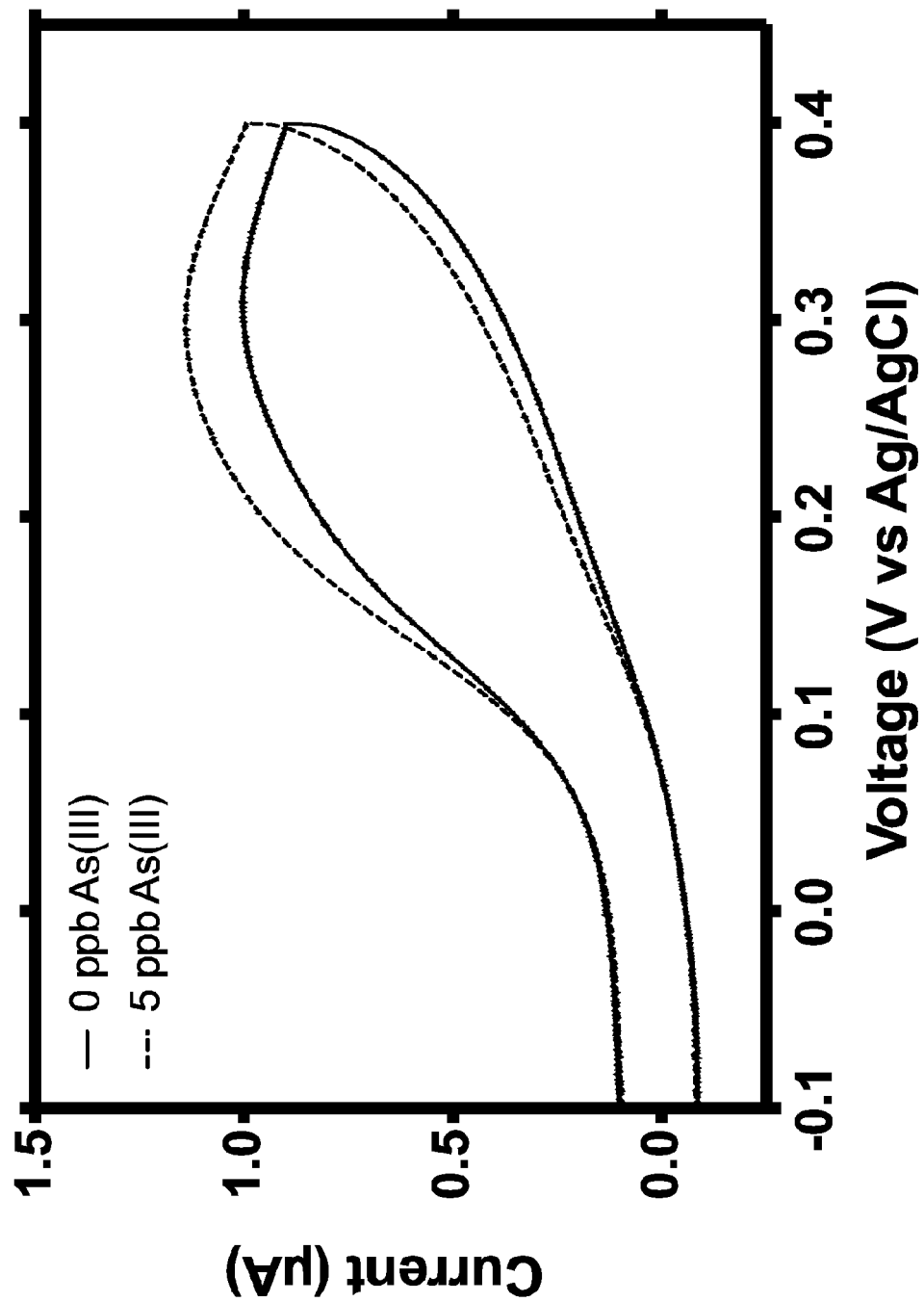

Example 6—Cyclic Voltammetric Detection of Arsenite in a Water Sample Using Bacterially Expressed β-galactosidase Controlled by an Arsenite Inducible Promoter and Using PNP as an Electroactive Analyte A cartridge 100 was constructed to include a voltammetric sensor 706 comprising a working carbon electrode, a working carbon counter electrode and a Ag/AgCl reference electrode. Cartridge 100 was then prepared to contain 0.16 ml of a 5 mM para-nitrophenol-β-D-glucuronide (PNPG) solution in 0.2M pH 7 sodium phosphate buffer in two of the bottom compartments 170 of sample reservoirs 135*a* and 135*b* of cartridge 100. The solution was left to evaporate and form a crystalline residue. A total volume of 200 μL of a liquid culture of *Escherichia coli* containing an As(III)-inducible β-galactosidase expression plasmid was introduced into each of the top compartments 165 of sample reservoirs 135*a*, and 135*b* of cartridge 100. Using a fluid collection device, substantially similar to fluid collection device 200, two 800 μL water samples containing 0 parts per billion (ppb) or 5 ppb As (III), respectively, were introduced into each bottom compartment 170 of sample reservoirs 135*a*, and 135*b* of cartridge 100 following piercing of each penetrable barrier 190. Cartridge 100 was then briefly shaken to ensure mixing of the *E. coli* culture, the water samples and PNPG and the mixture was left to incubate, to thereby allow for induction of β-galactosidase expression by As(III) and degradation of PNPG to form paranitrophenol (PNP). Thereafter, cartridge 100 was operably placed in a cartridge holder 520*a* of a voltammetric detection device 500, and a voltage was applied in a cyclical voltammetric fashion at 50 mV/s from −1 V to +0.4 V across a carbon counter electrode versus an Ag/AgCl reference electrode, and measurements were made using a carbon working electrode with respect to the reference electrode. Voltammetric graphs were prepared for each sample and are shown in FIG. 14. It is noted that the maximum value of the voltammetric current obtained using the water sample containing 5 ppb of As(III) exceeds the maximum value of the voltammetric current obtained using the water sample containing 0 ppb of As(III).

Figure 15:
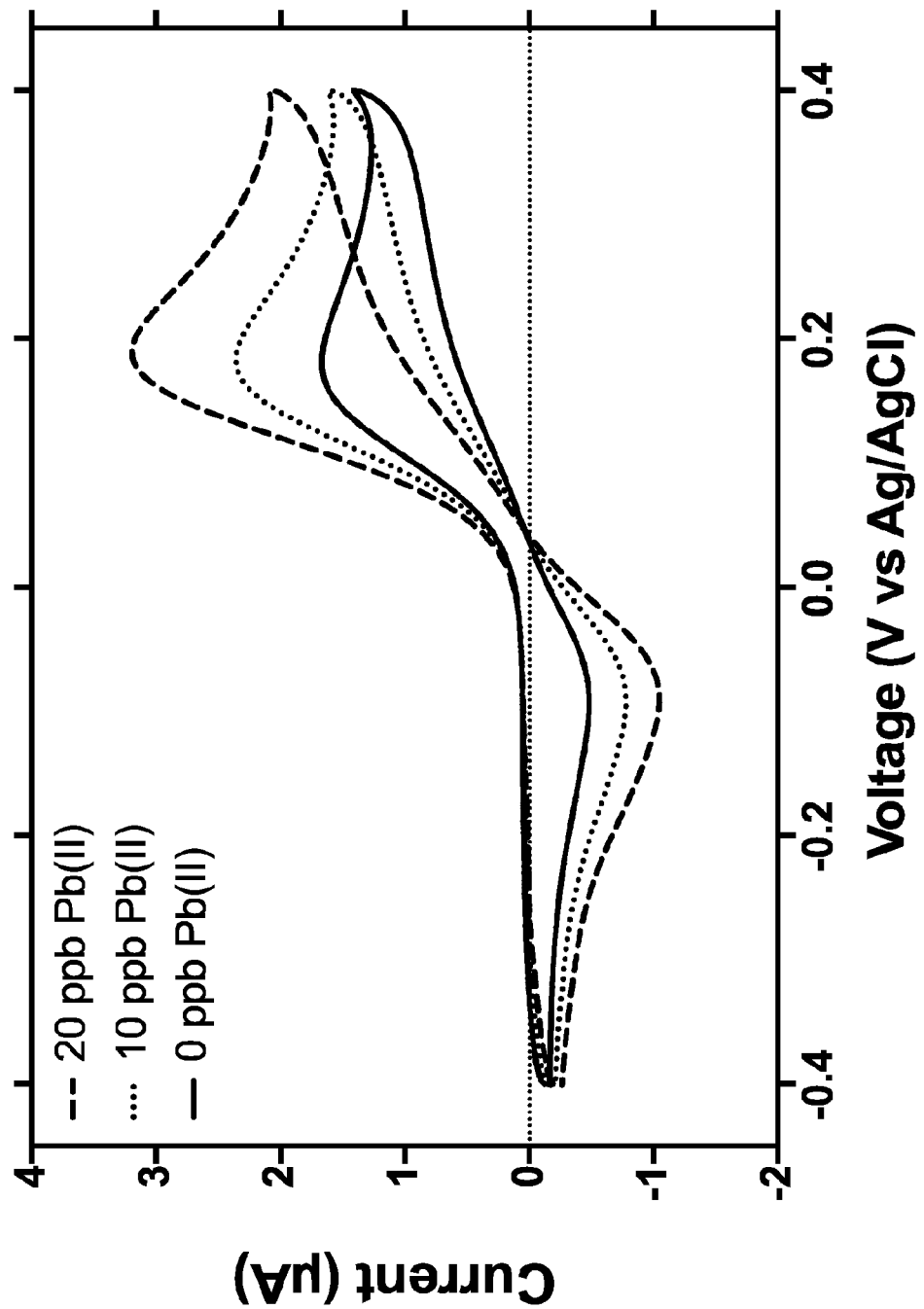

Example 7—Cyclic Voltammetric Detection of Lead Ions in a Water Sample Using Bacterially Expressed β-galactosidase Controlled by a Lead Ion Inducible Promoter and Using PAP as an Electroactive Analyte A cartridge 100 was constructed to include a voltammetric sensor 706 comprising a working carbon electrode, a working carbon counter electrode and a Ag/AgCl reference electrode. Cartridge 100 was then prepared to contain 0.16 ml of a 5 mM para-aminophenol-β-galactopyranoside (PAPG) solution in 0.2M pH 7 sodium phosphate buffer in each of the bottom compartments 170 of sample reservoirs 135a, 135b and 135c of cartridge 100. The solution was left to evaporate and form a crystalline residue. A total volume of 200 µL of a liquid culture of Escherichia coli containing an Pb(II)-inducible β-galactosidase expression plasmid was introduced into each of the top compartments 165 of sample reservoirs 135a, 135b and 135c of cartridge 100. Using a fluid collection device, substantially similar to fluid collection device 200, three 800 µL water samples containing 0 parts per billion (ppb), 10 ppb, or 20 ppb Pb(II), respectively, were introduced into each bottom compartment 170 of sample reservoirs 135a, 135b and 135c of cartridge 100 following piercing of each penetrable barrier 190. Cartridge 100 was then briefly shaken to ensure mixing of the E. coli culture, the water samples, and PAPG, and the mixture was left to incubate to thereby allow for induction of β-galactosidase expression by Pb(II) and degradation of PAPG to form para-aminophenol (PAP). Thereafter, cartridge 100 was operably placed in a cartridge holder 520a of a voltammetric detection device 500, and a voltage was applied in a cyclical voltammetric fashion at 50 mV/s from −0.4 V to +0.4 V across a carbon counter electrode versus an Ag/AgCl reference electrode, and measurements were made using a carbon working electrode with respect to the reference electrode. Voltammetric graphs were prepared for each sample and are shown in FIG. 15. It is noted that the maximum value of the voltammetric current obtained using the water sample containing 20 ppb of Pb(II) exceeds the maximum value of the voltammetric current obtained using the water sample containing 10 ppb of Pb(II), which, in turn, exceeds the maximum value of the voltammetric current obtained using the water sample containing 0 ppb of Pb(II).

Figure 16:
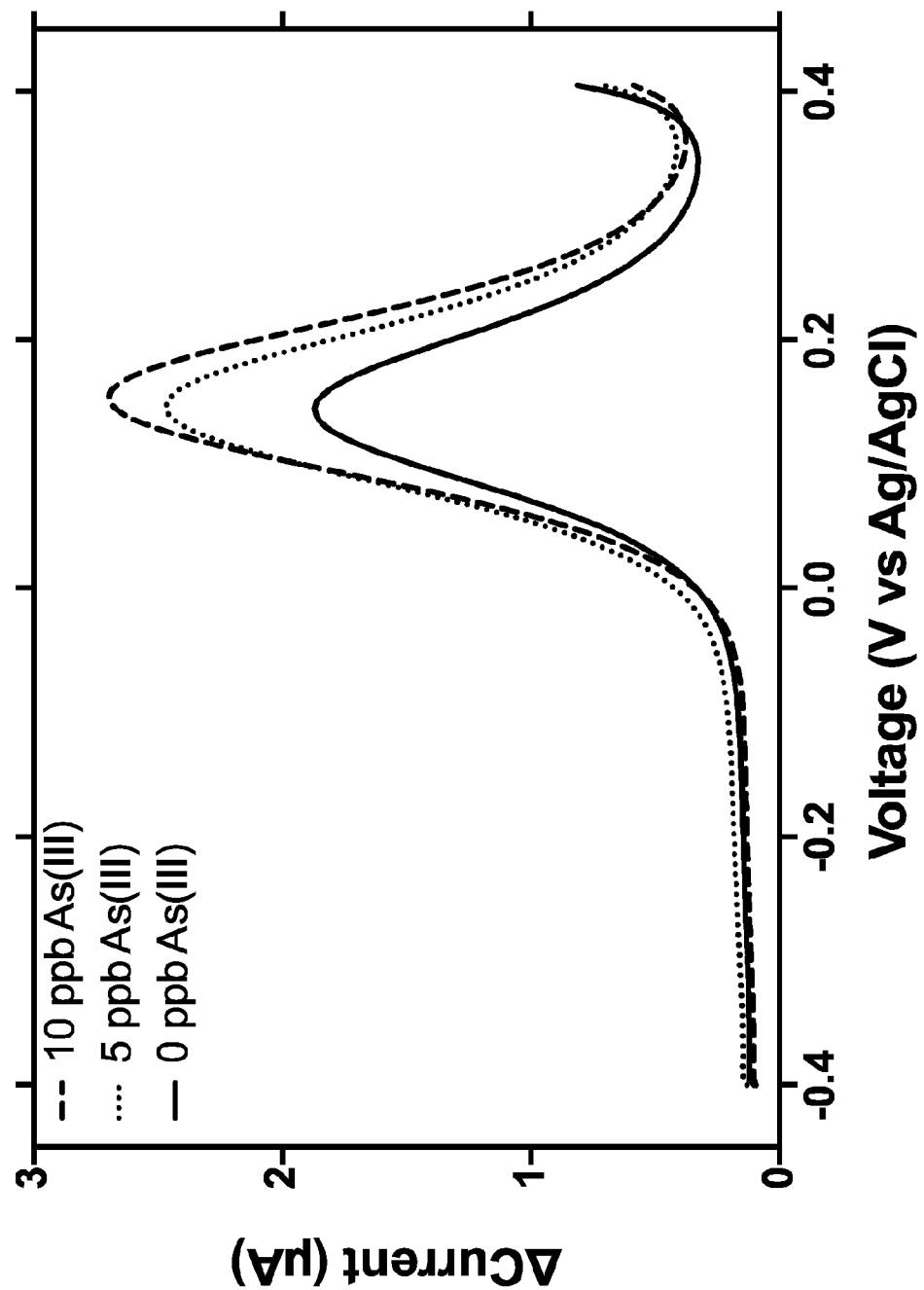

Example 8—Square Wave Voltammetric Detection of Arsenite in a Water Sample Using Bacterially Expressed β-galactosidase Controlled by an Arsenite Inducible Promoter and Using PAP as an Electroactive Analyte A cartridge 100 was constructed to include a voltammetric sensor 706 comprising a working carbon electrode, a working carbon counter electrode and a Ag/AgCl reference electrode. Cartridge 100 was then prepared to contain 0.16 ml of a 5 mM para-aminophenol-β-galactopyranoside (PAPG) solution in 0.2M pH 7 sodium phosphate buffer in each of the bottom compartments 170 of sample reservoirs 135a, 135b and 135c of cartridge 100. The solution was left to evaporate and form a crystalline residue. A total volume of 200 µL of a liquid culture of Escherichia coli containing an As(III)-inducible β-galactosidase expression plasmid was introduced into each of the top compartments 165 of sample reservoirs 135a, 135b and 135c of cartridge 100. Using a fluid collection device, substantially similar to fluid collection device 200, three 800 µL water samples containing 0 parts per billion (ppb), 5 ppb, or 10 ppb As (III), respectively, were introduced into each bottom compartment 170 of sample reservoirs 135a, 135b and 135c of cartridge 100 following piercing of each penetrable barrier 190. Cartridge 100 was then briefly shaken to ensure mixing of the E. coli culture, the water samples, and PAPG, and the mixture was left to incubate, to thereby allow for induction of β-galactosidase expression by As(III) and degradation of PAPG to form para-aminophenol (PAP). Thereafter, cartridge 100 was operably placed in a cartridge holder 520a of a voltammetric detection device 500, and a voltage was applied in a square wave voltammetric fashion at performed from −0.4 V to +0.4 across a carbon counter electrode versus an Ag/AgCl reference electrode, with a step height of 5 mV, pulse height of 25 mV and pulse width of 50 ms. Measurements were made using a carbon working electrode with respect to the reference electrode. Voltammetric graphs were prepared for each sample and are shown in FIG. 16. It is noted that the maximum value of the voltammetric current obtained using the water sample containing 10 ppb of As(III) exceeds the maximum value of the voltammetric current obtained using the water sample containing 5 ppb of As(III), which, in turn, exceeds the maximum value of the voltammetric current obtained using the water sample containing 0 ppb of As(III).

Example 9—Square Wave Voltammetric Detection of Lead Ions in a Water Sample Using Bacterially Expressed β-galactosidase Controlled by a Lead Ion Inducible Promoter and Using PAP as an Electroactive Analyte A cartridge 100 was constructed to include a voltammetric sensor 706 comprising a working carbon electrode, a working carbon counter electrode and a Ag/AgCl reference electrode. Cartridge 100 was then prepared to contain 0.16 ml of a 5 mM para-aminophenol-β-galactopyranoside (PAPG) solution in 0.2M pH 7 sodium phosphate buffer in each of the bottom compartments 170 of sample reservoirs 135a, 135b and 135c of cartridge 100. The solution was left to evaporate and form a crystalline residue. A total volume of 200 µL of a liquid culture of Escherichia coli containing an Pb(II)-inducible β-galactosidase expression plasmid was introduced into each of the top compartments 165 of sample reservoirs 135a, 135b and 135c of cartridge 100. Using a fluid collection device, substantially similar to fluid collection device 200, three 800 µL water samples containing 0 parts per billion (ppb), 10 ppb, or 20 ppb Pb (II), respectively, were introduced into each bottom compartment 170 of sample reservoirs 135a, 135b and 135c of cartridge 100 following piercing of each penetrable barrier 190. Cartridge 100 was then briefly shaken to ensure mixing of the E. coli culture, the water samples, and PAPG, and the mixture was left to incubate, to thereby allow for induction of β-galactosidase expression by Pb(II) and degradation of PAPG to form para-aminophenol (PAP). Thereafter, cartridge 100 was operably placed in a cartridge holder 520a of a voltammetric detection device 500, and a voltage was applied in a square wave voltammetric fashion at performed from −0.4

Figure 17:
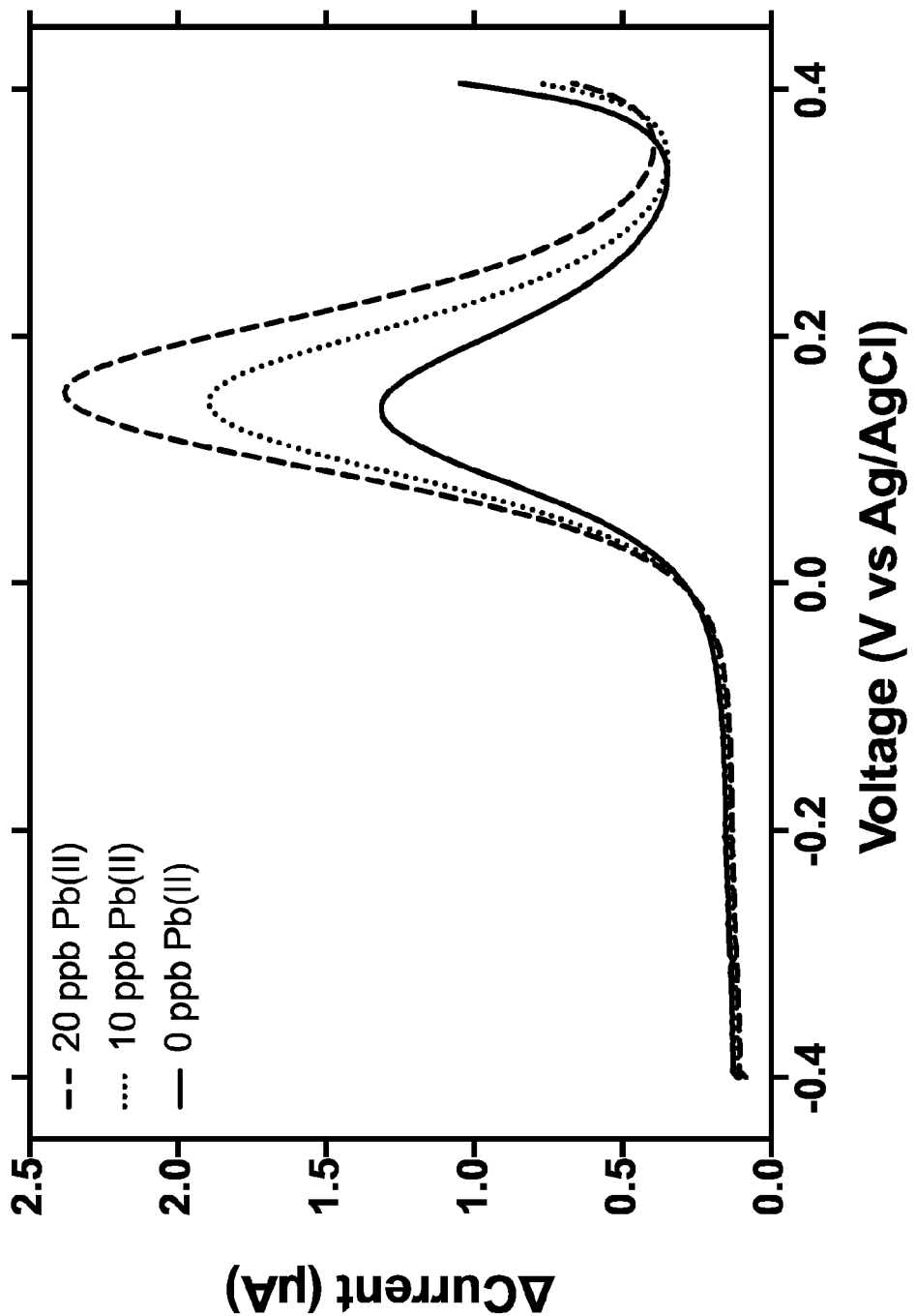

V to +0.4 V across a carbon counter electrode versus an Ag/AgCl reference electrode, with a step height of 5 mV, pulse height of 25 mV and pulse width of 50 ms. Measurements were made using a carbon working electrode with respect to the reference electrode. Voltammetric graphs were prepared for each sample and are shown in FIG. 17. It is noted that the maximum value of the voltammetric current obtained using the water sample containing 20 ppb of Pb(II) exceeds the maximum value of the voltammetric current obtained using the water sample containing 10 ppb of Pb(II), which, in turn, exceeds the maximum value of the voltammetric current obtained using the water sample containing 0 ppb of Pb(II).

Figure 18:
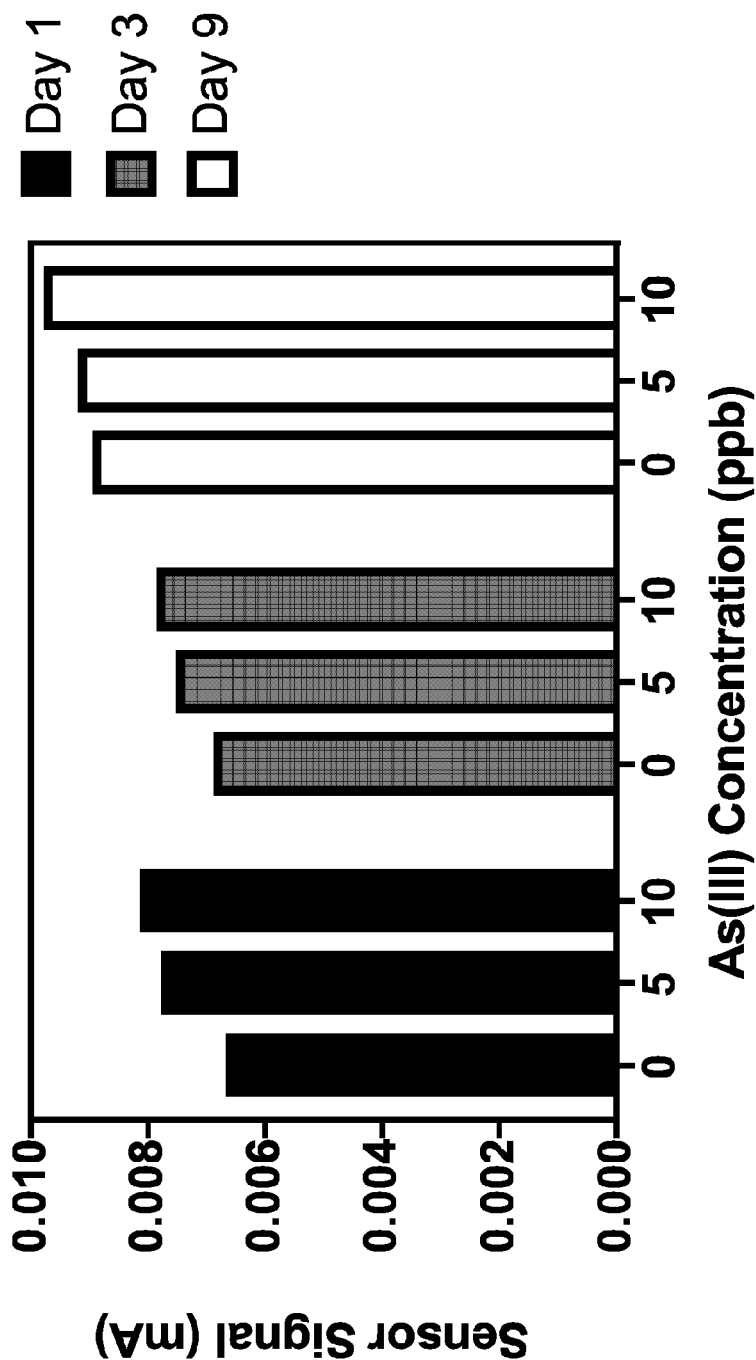
FIG. 18 is another bar graph illustrating experimental results obtained using an example embodiment of a cartridge and a voltammetric detection device of the present disclosure.

Example 10—Evaluation of the Effect of Cartridge Storage Time on Bacterial Cells Expressing β-galactosidase Using PAP as an Electroactive Analyte Three cartridges 100 were constructed to include a voltammetric sensor 706 comprising a working carbon electrode, a working carbon counter electrode and a Ag/AgCl reference electrode, and stored for a storage period of 1 day, 3 days, and 9 days, respectively. Each of the three cartridges 100 was then prepared to contain 0.16 ml of a 5 mM of a para-aminophenol-β-galactopyranoside (PAPG) solution in 0.2M pH 7 sodium phosphate buffer in each of the bottom compartments 170 of sample reservoirs 135a, 135b and 135c of cartridge 100. The solution was left to evaporate and form a crystalline residue. A total volume of 200 µL of a liquid culture of *Escherichia coli* containing an As(III)-inducible β-galactosidase expression plasmid was introduced into each of the top compartments 165 of sample reservoirs 135a, 135b and 135c of each of the three cartridges 100. Following the storage period, using a fluid collection device, substantially similar to fluid collection device 200, three 800 µL water samples containing 0 parts per billion (ppb), 5 ppb, or 10 ppb As (III), respectively, were introduced into each bottom compartment 170 of sample reservoirs 135a, 135b and 135c of cartridge 100 following piercing of each penetrable barrier 190. Each of the three cartridges 100 was then briefly shaken to ensure mixing of the *E. coli* culture, the water samples, and PAPG, and the mixture was left to incubate, to thereby allow for induction of β-galactosidase expression by As(III) and degradation of PAPG to form para-aminophenol (PAP). Thereafter, each of the three cartridge 100 was operably placed in a cartridge holder 520a of a voltammetric detection device 500, and a voltage was applied in a cyclical voltammetric fashion at 50 mV/s from −0.4 V to +0.4 V across a carbon counter electrode versus an Ag/AgCl reference electrode, and measurements were made using a carbon working electrode with respect to the reference electrode. Voltammetric graphs were prepared for each sample and the maximum value of the voltammetric current detected was recorded for each concentration of As (III) for each storage period. A bar graph with the results is shown in FIG. 18. It is noted that for each storage period, i.e. 1 day, 3 days, and 9 days, the maximum value of the voltammetric current detected using the water sample containing 10 ppb of As(III) exceeds the maximum value of the voltammetric current detected using the water sample containing 5 ppb of As(III), which, in turn, for each storage period, exceeds the voltammetric peak obtained using the water sample containing 0 ppb of As(III). Further it was noted that the current detected after 9 days of storage was not significantly greater than that detected after 1 day of storage, reflecting the lack of a reaction between the microbial cells in each top compartment with the PAPG in the bottom compartment.

The invention claimed is:

1. A sample analysis cartridge for the voltammetric detection of a fluid parameter in a fluid sample, the sample cartridge being releasably insertable in a voltammetric detection device, and comprising:
at least one sample analysis reservoir operable to receive an end portion of a fluid collection device that is used for the releasable collection of the fluid sample, the sample analysis reservoir comprising:
a first compartment containing an activating compound or an electroactive analyte that is activatable by the activating compound when the activated compound is activated by the fluid parameter in the fluid sample to form an activated electroactive analyte, the first compartment having an opening at an upper end;
a second compartment containing the electroactive analyte that is activatable by the activated activating compound to form the activated electroactive analyte when the first compartment contains the activating compound, or the second compartment contains the activating compound when the first compartment contains the electroactive analyte; and
a penetrable barrier disposed between the first and second compartments to fluidically separate the first and second compartment; and
a voltammetric sensor disposed at least partially within the second compartment.

2. A sample analysis cartridge according to claim 1, wherein during use, (i) when the sample fluid is in the sample analysis reservoir and makes contact with the activating compound, the fluid parameter in the fluid sample activates the activating compound and when the barrier is ruptured thereafter the activated activating compound contacts the electroactive analyte to form the activated electroactive analyte which in turn generates an electrical signal that is detected by the voltammetric sensor allowing the presence of the fluid parameter to be detected when a voltage is applied across the sample analysis reservoir, or (ii) when the first compartment contains the electroactive analyte and the sample fluid is in the sample analysis reservoir and the barrier is ruptured thereafter the fluid parameter in the fluid sample activates the activating compound in the second compartment, the activated activating compound then contacts the electroactive analyte to form the activated electroactive analyte which in turn generates an electrical signal that is detected by the voltammetric sensor allowing the presence of the fluid parameter to be detected when the voltage is applied to the voltammetric sensor, wherein during use the barrier is ruptured by the end portion of the fluid collection device.

3. A sample analysis cartridge according to claim 1, wherein the cartridge comprises a cartridge housing comprising a bottom housing portion and a top housing portion, the first compartment being disposed within the top housing portion and the second compartment being disposed within the bottom housing portion.

4. A sample analysis cartridge according to claim 1, wherein the cartridge comprises a cartridge housing comprising a bottom housing portion, the penetrable barrier being disposed within the bottom housing portion to form the second compartment; and a top housing portion that is slidably coupled to the bottom housing portion to form the first compartment.

5. A sample analysis cartridge according to claim 1, wherein the cartridge includes a second penetrable barrier, the second penetrable barrier being disposed over the opening of the first compartment and comprising a material for allowing an end portion of a fluid collection device, upon sufficient forceful engagement, to penetrate therethrough and be received by the first compartment to deliver the sample fluid thereto.

6. A sample analysis cartridge according to claim 1, wherein the sample analysis reservoir comprises a slot between the first and second compartments to slidably receive the penetrable barrier and separate the first and second compartments.

7. A sample analysis cartridge according to claim 1, wherein the penetrable barrier separating the first and second compartments comprises a divot, wherein the divot contains the activating compound or the electroactive analyte.

8. A sample analysis cartridge according to claim 1, wherein the penetrable barrier separating the first and second compartments is fabricated from a material that is tearable, shatterable or pierceable by the end portion of the fluid collection device.

9. A sample analysis cartridge according to claim 1, wherein the cartridge contains two, three, four, five or six sample reservoirs, wherein at least two different sample reservoirs are used to detect at least two different fluid parameters or at least two different sample reservoirs are used to detect identical fluid parameters.

10. A sample analysis cartridge according to claim 1, wherein the activating compound is a compound which in prolonged contact with the electroactive analyte causes sufficient activation of the electroactive analyte to be voltammetrically detectable in the absence of a fluid parameter from the sample fluid.

11. A sample analysis cartridge according to claim 1, wherein the activating compound is an activating polypeptide formed by cells contained in the first compartment, the cells comprising a promoter inducible by the fluid parameter and controlling the expression of an activating polypeptide.

12. A sample analysis cartridge according to claim 11, wherein the cells comprise microbial cells including bacterial cells or yeast cells and the microbial cells are in a liquid form, a dry form or a gel form.

13. A sample analysis cartridge according to claim 12, wherein the microbial cells comprise spore cells, *Escherichia* cells or *Bacillus* cells.

14. A sample analysis cartridge according to claim 11, wherein the cells comprise microbial cells, and the activating polypeptide is a hydrolase or a phosphatase, and the hydrolase is selected from the group consisting of a β-galactosidase, β-glucuronidase and β-glucosidase.

15. A sample analysis cartridge according to claim 1, wherein the fluid parameter being detected is a physical property, a toxic chemical substance or a chemical substance where the chemical substance includes an organic chemical compound or an inorganic chemical compound.

16. A method of voltammetrically detecting a fluid parameter in a fluid, the method comprising:
providing a fluid sample comprising a fluid parameter, the fluid sample being releasably collectable in a fluid collection device;
inserting an end portion of the fluid collection device into a cartridge comprising:
at least one sample analysis reservoir operable to receive the end portion of a fluid collection device, the sample analysis reservoir comprising:
a first compartment containing an activating compound or an electroactive analyte that is activatable by the activating compound when the activated compound is activated by the fluid parameter in the fluid sample to form an activated electroactive analyte, the first compartment having an opening at an upper end;
a second compartment containing the electroactive analyte that is activatable by the activating compound to form the activated electroactive analyte when the first compartment contains the activating compound, or the second compartment containing the activating compound when the first compartment contains the electroactive analyte; and
a penetrable barrier disposed between the first and second compartments to fluidically separate the first and second compartment; and
a voltammetric sensor disposed at least partially within the second compartment;
moving the end portion of the fluid collection device into the first compartment and penetrating the barrier with the end portion of the fluid collection device to fluidically connect the first and second compartment;
releasing the fluid sample from the fluid collection device into the sample analysis reservoir causing the fluid parameter to activate the activating compound to create the activated activating compound which then contacts the electroactive analyte to form the activated electroactive analyte which then contacts the voltammetric sensor;
applying a voltage to the voltammetric sensor;
detecting a current passing through the voltammetric sensor; and
comparing the detected current to a threshold to determine a presence the fluid parameter in the fluid sample.

17. A method of voltammetrically detecting a fluid parameter in a fluid according to claim 16, wherein the fluid sample is released in the first compartment prior to penetrating the barrier when the first compartment contains the activating compound or wherein the fluid sample is released in the second compartment after penetrating the barrier when the second compartment contains the activating compound.

18. A method of voltammetrically detecting a fluid parameter in a fluid according to claim 16, wherein the first compartment contains a second penetrable barrier being disposed over the opening, and the method comprises moving the fluid collection device sufficiently forcefully to penetrate the second barrier and move into the first compartment.

19. A method of manufacturing a sample analysis cartridge for the voltammetric detection of a fluid parameter in a fluid sample, the method comprising:
forming one or more sample reservoirs for the sample analysis cartridge where each sample reservoir is made by:
forming a bottom cartridge housing portion having a voltammetric sensor disposed therein;
placing an electroactive analyte or an activating compound in the bottom cartridge housing portion;
forming a top cartridge housing portion;
forming a penetrable barrier to separate the bottom and top cartridge housing portions;
placing an activating compound in the top cartridge housing portion when the electroactive analyte is placed in the bottom cartridge housing portion, or placing the electroactive analyte in the top cartridge housing portion when the activating compound is placed in the bottom cartridge housing portion; and (a) placing the penetrable barrier in the top portion of the bottom cartridge housing portion; and
slidably coupling the bottom and top cartridge housing portions to thereby form a cartridge;
or
(b) slidably coupling the bottom and top cartridge housing portions to thereby form a cartridge comprising a slot between the bottom and top cartridge portions to slidably receive the penetrable barrier; and
slidably inserting the penetrable barrier in the slot.

20. A voltammetric detection device for detecting a fluid parameter in a fluid sample contained in a sample analysis cartridge, the voltammetric detection device comprising:
at least one insertion slot for the releasable insertion of the sample analysis cartridge, the sample analysis cartridge being defined according to claim 1;
a voltage source configured to apply a voltage to a voltammetric sensor in a reservoir of the sample analysis cartridge;
a current detector for detecting a current passing through the voltammetric sensor upon application of the voltage to the sensor; and
a controller that is operatively coupled to the voltage source and the current detector and is configured to control the operation of the voltammetric detection device.

\* \* \* \* \*